United States Patent
Hofmeister et al.

(10) Patent No.: US 9,846,077 B2
(45) Date of Patent: Dec. 19, 2017

(54) DEVICES AND METHODS FOR ANALYZING GRANULAR SAMPLES

(71) Applicant: H2Optx Inc., San Jose, CA (US)

(72) Inventors: Rudolf J. Hofmeister, San Jose, CA (US); Donald A. Ice, Milpitas, CA (US); Scott W. Tandy, Los Altos Hills, CA (US)

(73) Assignee: H2OPTX INC., San Jose, CA (US)

( * ) Notice: Subject to any disclaimer, the term of this patent is extended or adjusted under 35 U.S.C. 154(b) by 0 days.

(21) Appl. No.: 14/744,778

(22) Filed: Jun. 19, 2015

(65) Prior Publication Data

US 2016/0216288 A1    Jul. 28, 2016

Related U.S. Application Data

(60) Provisional application No. 62/108,003, filed on Jan. 26, 2015.

(51) Int. Cl.

| | |
|---|---|
| *B07C 5/00* | (2006.01) |
| *G01J 3/42* | (2006.01) |
| *G01J 3/44* | (2006.01) |
| *G01J 3/06* | (2006.01) |
| *G01J 3/10* | (2006.01) |
| *B01D 46/00* | (2006.01) |
| *B01D 46/42* | (2006.01) |
| *G01N 1/06* | (2006.01) |
| *G01N 21/25* | (2006.01) |
| *G01N 33/15* | (2006.01) |

(Continued)

(52) U.S. Cl.
CPC ............ *G01J 3/42* (2013.01); *B01D 46/0002* (2013.01); *B01D 46/42* (2013.01); *G01J 3/00* (2013.01); *G01J 3/06* (2013.01); *G01J 3/10* (2013.01); *G01J 3/44* (2013.01); *G01N 1/06* (2013.01); *G01N 21/01* (2013.01); *G01N 21/25* (2013.01); *G01N 21/253* (2013.01); *G01N 21/33* (2013.01); *G01N 21/3504* (2013.01); *G01N 21/3577* (2013.01); *G01N 21/65* (2013.01); *G01N 23/00* (2013.01); *G01N 33/15* (2013.01); *G01N 35/10* (2013.01); *G01N 2021/0106* (2013.01)

(58) Field of Classification Search
CPC ........ G01J 3/00; G01J 3/06; G01J 3/10; G01J 3/42; G01J 3/44
USPC ................... 209/576, 577, 579, 580
See application file for complete search history.

(56) References Cited

U.S. PATENT DOCUMENTS

| | | | | |
|---|---|---|---|---|
| 3,435,540 A | * | 4/1969 | Sanders, Jr. .......... | F26B 17/122 34/174 |
| 3,499,144 A | * | 3/1970 | Juillet ..................... | G01N 1/20 264/109 |

(Continued)

FOREIGN PATENT DOCUMENTS

WO    2004/031749 A2    4/2004

*Primary Examiner* — Terrell Matthews

(57) ABSTRACT

In some aspects, a device for apportioning granular samples includes a sample feeder defining a conduit, the conduit including a first opening to receive the granular samples and a second opening. The device includes a shuttle operably coupled to the sample feeder to receive the granular samples from the conduit via the second opening. The shuttle is configured to apportion the granular samples to incrementally enter a sample chamber to be analyzed. The device includes an outlet conduit fluidly coupled to the sample chamber and configured to permit the sample chamber to be evacuated.

16 Claims, 23 Drawing Sheets

(51) Int. Cl.
    *G01N 21/01*     (2006.01)
    *G01N 23/00*     (2006.01)
    *G01N 35/10*     (2006.01)
    *G01N 21/3504*   (2014.01)
    *G01J 3/00*      (2006.01)
    *G01N 21/33*     (2006.01)
    *G01N 21/3577*   (2014.01)
    *G01N 21/65*     (2006.01)

(56) References Cited

U.S. PATENT DOCUMENTS

| | | | | |
|---|---|---|---|---|
| 3,822,866 | A * | 7/1974 | Daester | B01F 15/0445 366/8 |
| 4,863,040 | A * | 9/1989 | Sandi | B07C 5/344 193/31 A |
| 4,933,075 | A * | 6/1990 | Nordin | B07C 5/3416 209/576 |
| 4,963,743 | A * | 10/1990 | Satake | G01N 21/4738 250/339.07 |
| 5,408,846 | A * | 4/1995 | Reali | B02C 19/186 62/380 |
| 7,213,413 | B2 | 5/2007 | Battiste et al. | |
| 7,873,481 | B2 * | 1/2011 | Walk | G01N 30/8668 324/717 |
| 2005/0264813 | A1 | 12/2005 | Giakos | |
| 2006/0002594 | A1 | 1/2006 | Clarke et al. | |
| 2009/0002702 | A1 | 1/2009 | Maier et al. | |
| 2009/0010388 | A1 | 1/2009 | Stahly et al. | |
| 2012/0302892 | A1 | 11/2012 | Lue et al. | |
| 2015/0355083 | A1 * | 12/2015 | Marbach | B07C 5/3408 356/402 |

* cited by examiner

DEVICES AND METHODS FOR ANALYZING GRANULAR SAMPLES

CROSS-REFERENCE TO RELATED APPLICATIONS

This application claims priority to U.S. Patent Application No. 62/108,003, filed Jan. 26, 2015, entitled "SYSTEMS, DEVICES AND METHODS FOR ANALYZING AND PROCESSING SAMPLES," which is incorporated by reference in its entirety.

BACKGROUND

The present disclosure generally relates to systems, devices and methods for analyzing and processing samples. Information about the samples may be obtained through a variety of analysis techniques such as microscopy, spectroscopy, spectrometry, chromatography, as well as many others. Information about the samples may be used to conduct experiments; improve, control or monitor production processes; or improve, control or monitor manufactured products.

The claimed subject matter is not limited to embodiments that solve any disadvantages or that operate only in environments such as those described above. This background is only provided to illustrate examples of where the present disclosure may be utilized.

SUMMARY

The present disclosure generally relates to systems, devices and methods for analyzing and processing samples. Information about the samples may be obtained through a variety of analysis techniques such as microscopy, spectroscopy, spectrometry, chromatography, as well as many others. Information about the samples may be used to conduct experiments; improve, control or monitor production processes; or improve, control or monitor manufactured products.

In an example embodiment, a device for apportioning granular samples includes a sample feeder defining a conduit, the conduit including a first opening to receive the granular samples and a second opening. The device includes a shuttle operably coupled to the sample feeder to receive the granular samples from the conduit via the second opening. The shuttle is configured to apportion the granular samples to incrementally enter a sample chamber to be analyzed. The device includes an outlet conduit fluidly coupled to the sample chamber and configured to permit the sample chamber to be evacuated.

In another example embodiment, an evacuation subassembly is configured to separate portions of granular samples based on at least one characteristic of a component of the granular sample portions. The evacuation subassembly includes one or more vacuum elements configured to generate a pressure differential to evacuate a sample chamber fluidly coupled to the vacuum element. The evacuation subassembly includes a switch configured to selectively couple the one or more vacuums to one or more outlet channels to selectively evacuate the sample chamber into one or more outlet channels. The evacuation subassembly includes at least one receptacle fluidly coupled to the one or more outlet channels and configured to receive substances selectively evacuated from the sample chamber. The evacuation subassembly may be configured such that each of the granular sample portions positioned inside of the sample chamber is analyzed and selectively evacuated based on at least one characteristic of a component of each of the granular sample portions.

In further implementations, a method of analyzing granular samples includes providing granular samples to be analyzed. The method includes apportioning the granular samples into granular sample increments. The method includes incrementally analyzing each of the granular sample increments. The method includes actuating a shuttle to permit the granular sample increment to enter a sample chamber at least partially defined by an electromagnetically transmissive window. The method includes transmitting electromagnetic radiation from an emitter to incident the granular sample increment. The method includes moving a portion of an analyzation subassembly in one or more directions of movement with respect to the granular sample increment to scan at least a portion of the granular sample increment. The method includes receiving electromagnetic radiation from the granular sample increment by the analyzation subassembly through the window. The method includes identifying at least one characteristic of a component of the granular sample increment based on the electromagnetic radiation received from the granular sample increment. The method includes evacuating the granular sample increment from the sample chamber.

This Summary introduces a selection of concepts in a simplified form that are further described below in the Detailed Description. This Summary is not intended to identify key features or essential characteristics of the claimed subject matter, nor is it intended to be used as an aid in determining the scope of the claimed subject matter.

DETAILED DESCRIPTION

Figure 1:
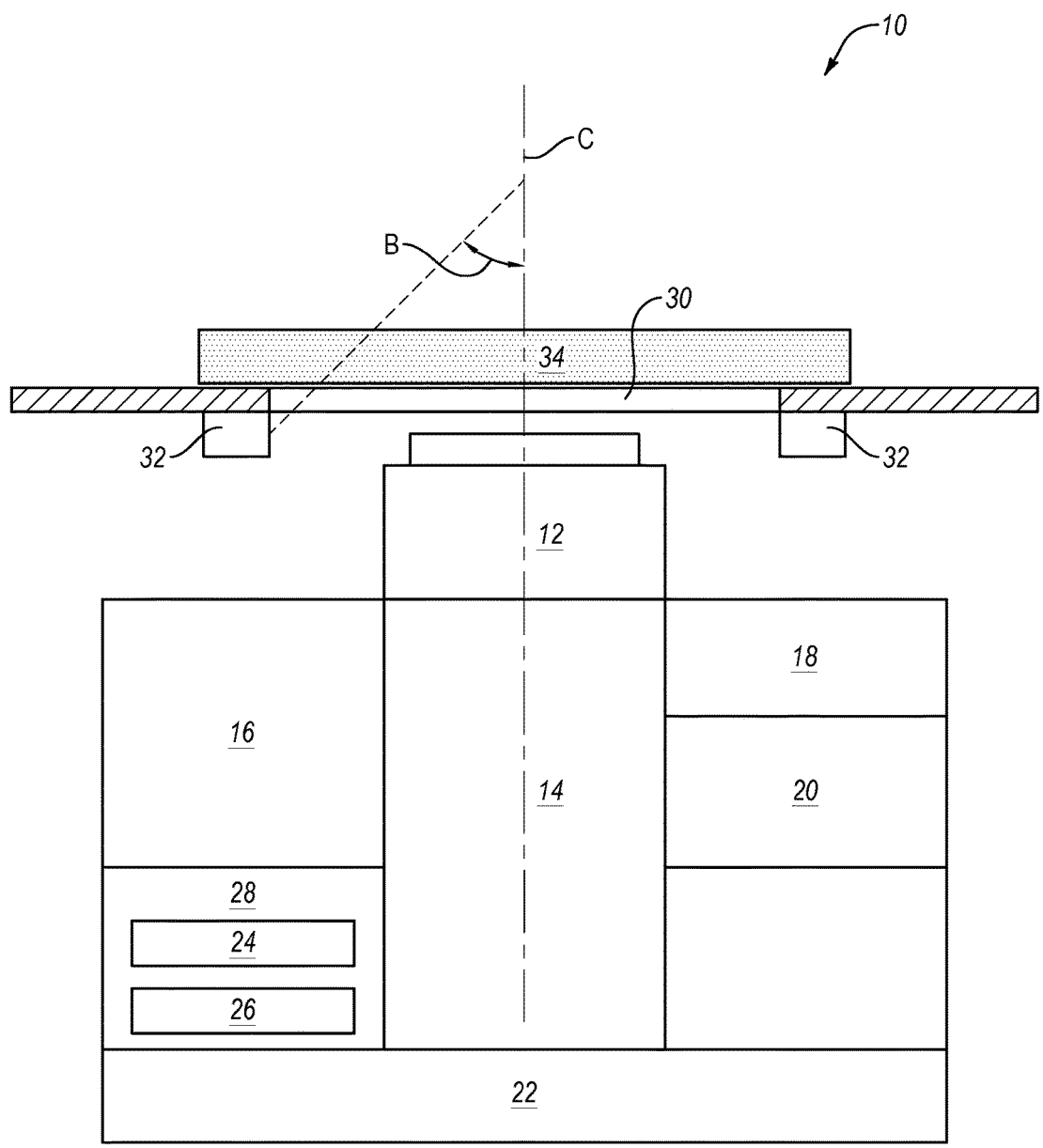
FIG. 1 is a schematic diagram of a non-limiting embodiment of a system configured to analyze or process samples.

Reference will be made to the drawings and specific language will be used to describe various aspects of the disclosure. Using the drawings and description in this manner should not be construed as limiting the scope of the disclosure. Additional aspects may be apparent in light of the disclosure, including the claims, or may be learned by practice. The drawings are non-limiting, diagrammatic, and schematic representations of example embodiments, and are not necessarily drawn to scale.

The terms and words used in the following description and claims are not limited to the bibliographical meanings, but, are merely used to enable a clear and consistent understanding of the disclosure. It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those skilled in the art, may occur in amounts that do not preclude the effect the characteristic was intended to provide.

The term "granular sample" may include single crystalline particles, polycrystalline particles, granulated particles, granulated multicomponent particles, micronized particles, single component or blended substances, or any combination thereof. In some aspects, "granular sample" may include any powdered sample.

The term "vacuum" may refer to a pressure differential in a system or a portion of a system. The term "vacuum" may include a positive or negative pressure differential. In some aspects, the term "vacuum" may refer to systems or portions of systems with an internal pressure less than or greater than atmospheric pressure.

The present disclosure generally relates to systems, devices and methods for analyzing and processing samples. The disclosed systems may include modular aspects that permit the systems to be configured to analyze or process different types of samples. Additionally or alternatively, the systems may include modular aspects to permit the systems to be configured to analyze or process samples by one or more different methods or techniques. Information about the samples may be obtained through a variety of analysis techniques such as microscopy, spectroscopy, spectrometry, chromatography, as well as many others. Information about the samples may be used to conduct experiments; improve, control or monitor production processes; or improve, control or monitor manufactured products.

In some configurations, the disclosed systems may be used in a lab setting to conduct experiments. For example, the configuration of the systems may be selected for powders, liquids, gases, emulsions, suspensions, solids, homogeneous combinations, heterogeneous combinations, pills, tablets, materials, biological samples, and/or any suitable combinations thereof.

In other configurations, the disclosed systems may be used as a part of production line to analyze and process samples to obtain information about aspects of the production line, such as characteristics of the finished products or intermediaries of the products. The disclosed systems may be implemented as in-process monitoring systems integrated into a production line and configured to analyze one or more properties of a sample as it is being produced.

FIG. 1 is a schematic diagram of an example embodiment of a system 10 that may be configured to analyze or process samples. The system 10 may include an objective 12 optically coupled to an optical multiplexer 14. The optical multiplexer 14 may be optically coupled to a sensor 16, an emitter 18 and/or a detector 20. A sample 34 may be positioned on and/or over a window 30 that is optically coupled to the objective 12 and/or the optical multiplexer 14. The system 10 may include a platform 22 that may be configured to move portions of the system 10 relative to the sample 34. In some configurations, the platform 22 may be configured to move portions of the system 10 in three directions of movement (linear, non-linear, angular, etc.). At least some portions of the system 10 can be translated in any of the three directions relative to the sample 34. In operation, the movement of the platform 22 may contribute to focusing optical components of the system 10, scanning the sample 34, engaging or disengaging portions of the system 10, and/or a combination thereof.

The emitter 18 may be configured to emit radiation to analyze the sample 34. The emitter may emit any suitable electromagnetic radiation to analyze and/or process the sample 34. For example, the emitter 18 may emit visible light, ultraviolet light, X-rays, infrared or any other suitable radiation. In some configurations, the emitter 18 may be a laser or diode. In some configurations, the emitter 18 may be a Raman laser source.

The detector 20 may be configured to detect radiation from the sample 34. For example, the detector 20 may be configured to detect radiation from the sample 34 resulting from the radiation from the emitter 18 incidenting the sample 34. The detected radiation may permit information regarding the sample 34 to be obtained. In some configurations, the detector 20 may be a Raman spectrometer.

An emitter 32 may be positioned around the window 30 and/or proximate the sample 34 and configured to emit radiation that may incident the sample 34. In some configurations, the emitter 32 may be a ring encircling the window 30. In other configurations, the emitter 32 may be one or more discrete emitter elements positioned at various suitable positions with respect to the window 30 and/or the sample 34. In some configurations, the emitter 32 may be an electromagnetic radiation source or an electromagnetic radiation ring.

In some configurations, the system 10 may include a controller 28 configured to control the operation of at least a portion of the system 10. The controller 28 may include a processor 24 that executes instructions stored in memory 26. The processor 24 and memory 26 can be incorporated into the system 10, as illustrated. In other configurations, the processor 24 and/or the memory 26 can be located in a controller 28 external to the system 10. For example, the system 10 may be controlled and/or operated by a computer system coupled to the system 10.

The memory 26 can include executable instructions that control the operation of the system 10. For example, the memory 26 can comprise instructions that when executed by the processor 24 causes the emitter 32 to expose the sample 34 to emitted radiation (e.g., electromagnetic, visible light, ultraviolet, heat, microwave, or other radiation). Depending on the properties of the sample 34 and the characteristics of the emitted radiation, some of the radiation projected on the sample 34 may pass through the sample 34, some may be absorbed by the sample 34, and/or some may be reflected by the sample 34.

Emissions from the irradiated sample 34 (for example, by reflection or fluorescence), may travel through the objective 12 into the optical multiplexer 14. At least a part of the emissions from the sample 34 may be directed to the sensor 16 by the optical multiplexer 14. The sensor 16 may detect characteristics of the received radiation, such as energy level, wavelength, or other characteristics. The characteristics of the received radiation may be used to determine characteristics of the sample 34. For example, in some configurations, the characteristics of the received radiation may be used to determine aspects of the sample 34.

The system 10 may be configured to use the sensor 16 to obtain information about the sample 34. For example, the sensor 16 may be an image sensor (e.g., a color camera, or monochromatic camera) configured to obtain images of the irradiated sample 34. The controller 28 may be configured to receive, process, modulate, and/or convert signals from the sensor 16 to obtain information about the sample 34. In some configurations, the controller 28 may be configured to generate images of the sample 34 from the signals from the sensor 16. The controller 28 can employ image analyzing algorithms to: (i) compare particle luminance magnitude of the sample 34; (ii) detect particle sizes of the sample 34; (iii) compare particle sizes against other sizes in the sample 34 or to a database of particle sizes; (iv) compare particle sizes against other shapes in the sample 34 or to databases of particle shapes, and/or any suitable combinations of these algorithms or others.

In some configurations, the emitter 32 emits electromagnetic radiation at a given wavelength of a plurality of wavelengths into the sample 34. The emitter 32 may include, for example, one or more emitters capable of producing electromagnetic radiation within a terahertz range. In another example, a wavelength of the electromagnetic radiation may be within a range of approximately 0.01 to 10 nanometers. This range comprises X-ray wavelengths. In yet another example, the electromagnetic radiation produced by the emitter 32 may be varied in wavelength from blue to ultraviolet light. In another example, the emitter 32 emits white light. The responsiveness of the sample 34 is determined by the controller 28 by examining color of the one or more of the components of the sample 34.

The emitter 32 may be multiple sources that each provides a unique narrow band wavelength of electromagnetic radiation. For example, each of the emitters 32 may output any of red, blue, and green light. The emitters 32 may include light emitting diodes and/or lasers.

In yet other configuration, the emitter 32 may expose the mixture sample to near infrared or mid infrared light. The emitters 32 may produce broad band radiation or successive bursts of narrow bands of radiation. In one example, the emitters 32 may selectively expose the mixture sample to many different wavelengths of electromagnetic radiation and analyzing how each wavelength affects components of the sample 34. This example configuration may be used to analyze samples of unknown composition, although other configurations are contemplated.

The objective 12 may include a high, low, or variable magnification objective lens. The objective 12 may include a high magnification lens that permits viewing of small particles (e.g., less than 20 microns in size) and/or viewing small features on larger particles. The objective 12 may include low magnification lenses used to provide a large field of view, which may permit rapid identification of regions of interest in an image. The magnification of the objective 12 may be selectively varied by the controller 28 to locate particles at low power settings. The controller 28 may be configured execute analytical processes to identify the particle by shape and/or size. The controller 28 may be configured to zoom in where particles of certain characteristics are identified.

In some configurations, an optical filter may be optically coupled prior to the sensor 16 to block frequencies of radiation that may damage the sensor 16 and/or provide undesired effects on the information obtained by the sensor 16. In some configurations, the optical filter may be selected depending on the wavelength of the electromagnetic radiation that is output by the emitter 32. In some configurations, the optical filter may be configured to block light at wavelengths of approximately 425 nanometers to 700 nanometers. In other configurations, higher wavelength filters may be used in combination with lower wavelength filters. For example, higher wavelength filters may be used, for example, with Raman lasers, while lower wavelength filters may be used with, for example, ultraviolet light. In some configurations, the emitter 32 may be a laser optically coupled with a long pass filter. In another example, the emitter 32 may be a light emitting diode (LED) optically coupled to a long pass filter.

The system 10 may include one or more optical filters used to block the excitation wavelength for the sensor 16 to permit the sensor 16 to obtain usable images. The controller 28 may be configured to activate the emitter 32 for a set period of time, such as ten seconds. Images may be captured of the sample 34 by the sensor 16 to determine the responsiveness of at least portions of the sample 34 by detecting timing and decay of response of the one or more of the components of the sample 34 to the radiation.

The system 10 may use additional measurement algorithms to detect and differentiate components of the sample 34 from one another using particle size and shape. For example, the controller 28 of the system 40 can use various image processing methods to determine an aspect ratio for particles of components of the sample 34. Also, the controller 28 of the system 10 can calculate size, shape, fuzziness, angularity, brightness, and combinations thereof for components of the sample 34.

The size and/or shape of components of the sample 34 may be used to detect the presence of paper fibers or other contaminates. For example, if a particle is detected, its size and shape may be calculated using image processing. The size and shape may be compared to a database of particle sizes and corresponding shapes. If no reasonable comparison is found, a particle may be determined to be a contaminate. Contaminates may be catalogued and/or stored in a database. In some configurations of the system 10, contaminants may be isolated, concentrated, separated, stored, and/or disposed, as will be described in further detail below with respect to FIGS. 9A-9D. The algorithm used by the controller 28 may be selected based on the composition of the sample 34, if an expected composition for the sample 34 is known.

With continued reference to FIG. 1, the emitter 32 may emit electromagnetic radiation into the mixture sample at an angle B that is specified with reference to a central axis C of the window 30. In such configurations, radiation may enter the sample 34 at the angle B.

The controller 28 may be configured to detect, track and/or count a number of excited particles in the sample 34. The controller 28 may be further configured to calculate a concentration of a selected component of the sample 34. For example, when the controller 28 has located a number of a first component of the sample 34, the controller 28 may calculate a volume of the first component of the sample 34, for example, using image analysis. The overall area of the particles of the first component relative to the total area of the image may be used to estimate the volume by weight of the first component, if the size of the first component particles is known.

In some configurations, Raman spectroscopy may be used to verify and/or analyze the presence, size, and/or shape of components of the sample 34. In such configurations, the emitter 18 may be a Raman laser source and the detector 20 may be a Raman spectrometer. The emitter 18 may be controlled, for example, by the controller 28 to expose the sample 34 to a wavelength of laser light. The laser light may be focused onto a small portion of the sample 34 where candidate particles are fluorescing (e.g., responsive). Images may be transferred by the optical multiplexer 14 to the Raman spectrometer detector 20 via a Raman spectrometer interface. The Raman spectrometer 20 and or the Raman spectrometer interface may be integrated into the system 10 or may be a standalone external feature. In some circumstances, the identification of the candidate particles may be confirmed using Raman spectroscopy.

In other configurations, the emitter 18 may instead be an X-ray source, near infrared source, infrared source, ultra violet source, and/or any source of radiation suitable for an intended application. The system 10 may include any suitable combinations or permutations of these or other radiation sources, depending on the type of analytes being analyzed and/or the desired information to be obtained.

In some configurations, the system 10 may be used to obtain three-dimensional models of the sample 34. A three dimensional model may be a composition of many images obtained using permutations of positions in three axes X, Y, and Z. For example, the objective 12 may be moved in three directions of movement along three axes X, Y, and Z by the platform 22. The Z-axis may be aligned with the central axis C of the window 30. Depending on the width of the field of view of the sensor 16, the objective 12 may be moved sequentially along the window 30 in the X and Y direction. At each X and Y location, the platform 22 may translate the objective 12 from an initial position along the Z-axis towards the window 30, in increments (e.g., one micron increments, etc.). At each increment, the sensor 16 may obtain an image of the illuminated sample 34. The system 10 may be capable of obtaining images at any given depth into the sample 34. These images may each be associated with their respective X, Y, and Z location information. The images may be assembled together by the system 10, for example via the controller 28, to form a three-dimensional model of the sample 34.

The three-dimensional imaging of the sample 34 may be used to calculate responsive particles of a component of the sample 34 on a surface of the sample 34, as well as particles located within the sample 34 at a specified distance inside the surface of the sample 34.

A method of analyzing the sample 34 using the system 10 will be described in further detail. The method may include capturing high resolution color images of the sample 34 exposed with multiple color lighting (e.g., a range of wavelengths of electromagnetic radiation). The multiple color lighting of the sample 34 may occur at multiple angles of incidence and/or from different directions. For example, the angle B may be selectively varied during illumination of the sample 34. The method may include processing the images to identify possible particles of a first component of the sample 34 by size, color, and/or shape. The method may include using Raman scanning and analysis to positively identify candidate particles as particles of the first component. This may be accomplished using a Raman signature for particles of the first component as a baseline. The method may include calculating a particle area to percentage-by-weight calculation where a percentage-by-weight is correlated to a percentage-by-area of particles of the first component observed in the images. The method may be repeated until a statistically significant particle area is located in one or more components of the sample 34 and/or multiple samples.

The system 10 may include any suitable aspects described in U.S. patent application Ser. No. 14/507,637, entitled "OPTICAL AND CHEMICAL ANALYTICAL SYSTEMS AND METHODS" and U.S. patent application Ser. No. 14/454,483, entitled "ANALYSIS AND PURGING OF MATERIALS IN MANUFACTURING PROCESSES," which are both incorporated by reference in their entirety and for all purposes. The concepts described with respect to the system 10 may be implemented in a variety of configurations and may be combined with other aspects of this disclosure, as may be indicated by context.

Turning to FIGS. 2A-2E, an example embodiment of a system 40 that can be configured to analyze or process samples will be described. In some configurations, the system 40 may be an implementation of the system 10 of FIG. 1. Accordingly, the system 40 may include any suitable aspects described with respect to system 10, as may be indicated by context.

Figure 2A:
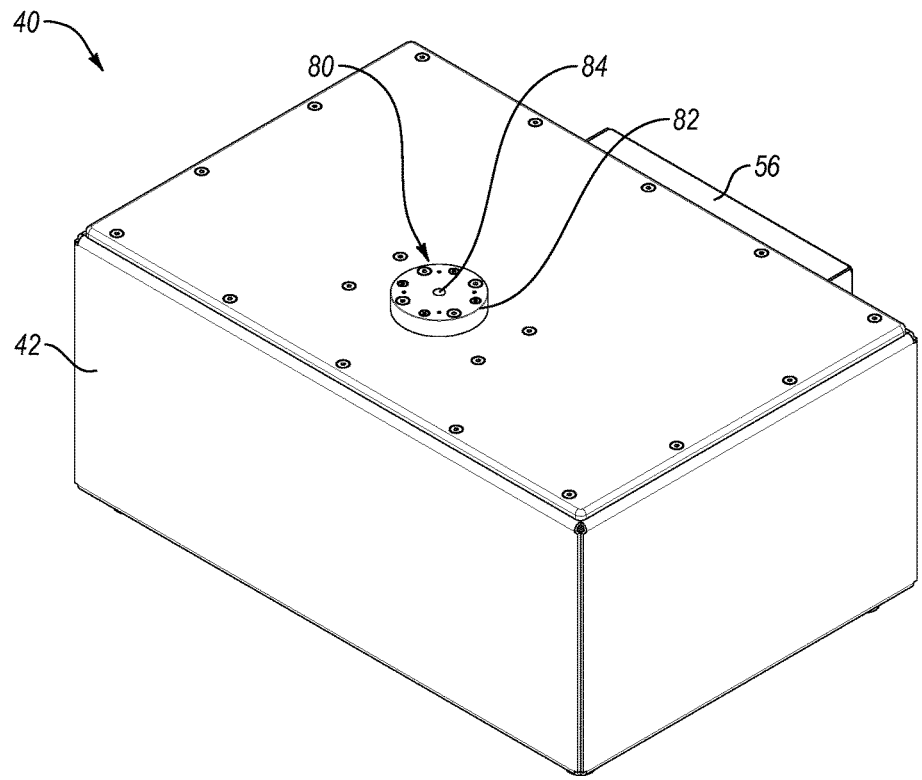
FIGS. 2A-2B are perspective views of a non-limiting embodiment of a system configured to analyze or process samples.
Figure 2B:
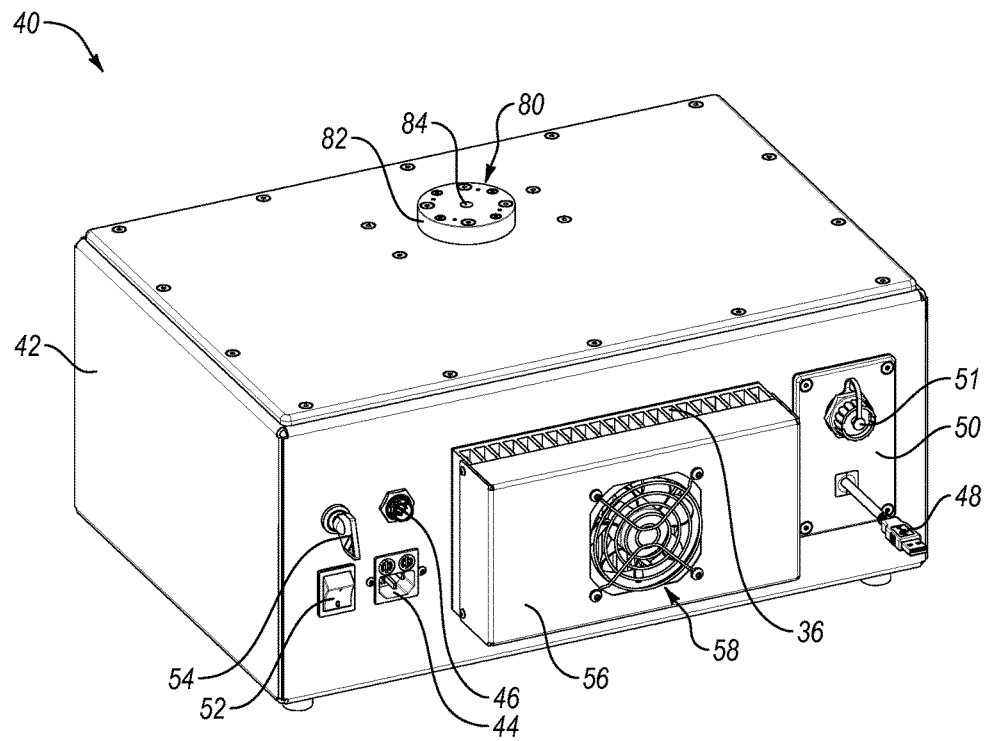

FIGS. 2A and 2B are perspective views of a portion of the system 40. As illustrated, the system 40 may include a housing 42 surrounding at least a portion of the system 40. The system 40 may include an interface assembly 80 configured to interface with other portions of the system 40, as will be described in further detail below. The interface assembly 80 may include a body 82 and a window 84 that is configured to permit light to travel through at least a portion of the interface assembly 80. The window 84 may be at least partially transparent or translucent and/or may be configured to convey, direct, collimate and/or focus light travelling through the interface assembly 80. In the illustrated configuration, the interface assembly 80 is positioned on a top portion of the housing 42, although other suitable configurations are contemplated.

Turning to FIG. 2B, the system 40 may include a first connector 44, a second connector 46, and a third connector 48 connecting portions of the system 40 inside of the housing 42 to portions of the system 40 exterior to the housing 42. The connectors 44, 46, and 48 may be electronic connectors configured to transmit data, power and/or control signals. The system 40 may include a switch 52 that may be configured to activate and/or turn on at least portions of the system 40.

As illustrated, the first connector 44 may be a socket configured to receive a first plug to electrically couple the system 40 and the second connector 46 may be a socket configured to receive a second plug to electrically couple the system 40. The first connector 44 may permit the system 40 to be electrically coupled to a power source, for example, an alternating current (AC) power supply. The second connector 46 may be a socket configured to transmit data, power and/or control signals in and/or out of portions of the system 40 inside of the housing 42.

As illustrated, the third connector 48 may be a cable connector coupled with the housing 42 by a connector panel 50. In the illustrated configuration, the third connector 48 is a Universal Serial Bus (USB) cable extending from the system 40. In such configurations, the third connector 48 may transmit one or more of data, power and/or control signals. In other configurations, the third connector 48 may be any suitable connector that may or may not correspond to an interface standard or interface protocol (such as USB, firewire, etc.). The connector panel 50 may include a connector 51 which may be, for example, a fluid connector or a vacuum connector.

In some configurations, the third connector 48 may permit the system 40 to be coupled to electronic components such as computers, computer systems, computer interfaces, user interfaces, mobile devices and/or any other suitable electronic component. In such configurations, the electronic component may provide power and/or control signals to the system 40 via the third connector 48. Additionally or alternatively, the electronic component may receive data signals and/or feedback from the system 40 via the third connector 48. In other configurations, the third connector 48 may permit the system 40 to be coupled to other components of the system 40. In such configurations, portions of the system 40 (for example, portions inside of the housing 42) may provide power and/or control signals to at least one other component of the system 40 via the third connector 48. Additionally or alternatively, portions of the system 40 (for example, portions inside of the housing 42) may receive data signals and/or feedback from at least one other component of the system 40 via the third connector 48. The connector panel 50 may be removably coupled to the housing 42 to permit connectors of different types to be coupled to the system 40.

In some configurations, the system 40 may include non-illustrated connectors such as a fluid connector configured to permit fluid (gaseous, liquid, or otherwise) to travel into or out of the housing 42. Fluid connectors may permit the system 40 to be coupled with, for example, vacuum lines, pressurized gas lines, cooling fluid lines, water lines, liquid lines, or other suitable fluids. Although the illustrated configuration includes three connectors 44, 46, and 48, the system 40 may include any suitable amount of connectors and may include connectors of any suitable type. The configurations of the connectors may be selected based on the desired configuration and/or functionality of the system 40, as applicable. Additionally or alternatively, the configuration of the connectors may be selected depending on modular components that may be coupled, added and/or activated with the system 40.

The system 40 may include a security assembly 54 that may be configured to lock the system 40 from being operated. For example, the security assembly 54 may disable portions of the system 40 such as emitters from operating to facilitate in preventing inadvertent exposure to electromagnetic radiation. In some configurations, the security assembly 54 may disconnect power from one or more emitters of the system 40. The security assembly 54 may facilitate in preventing operation of the system 40 in a potentially unsafe manner and/or may facilitate in preventing inadvertent exposure to electromagnetic radiation when the system 40 is being serviced. In the illustrated configuration, the security assembly 54 is a key and a lock configured to receive the key. In other configurations, the security assembly 54 may include any suitable electronic and/or mechanical locking mechanism. For example, biometric and/or cryptographic key locking mechanisms (password, passphrase, personal identification number, etc.) may be employed. The security assembly 54 may facilitate safe operation of the system 40 by permitting only qualified users to operate the system 40.

The system 40 may include a temperature management assembly 56 configured to facilitate temperature control of at least a portion of the system 40. For example, the temperature management assembly 56 may heat or cool portions of the system 40, such as those positioned within the housing 42, to maintain desired or suitable operating conditions. As illustrated for example in FIG. 2E, in some configurations the temperature management assembly 56 may include a heat sink 36 positioned between a first ventilator 38 and a second ventilator 58. The heat sink 36 may be configured to transmit heat by conduction and maintain separation between the interior and the exterior of the housing 42. The first ventilator 38 and second ventilator 58 may be configured to drive air and/or other fluids along the surfaces of the heat sink 36 to facilitate heat management. In other configurations, the temperature management assembly 56 may include any suitable heating and/or cooling mechanisms.

Although in the illustrated configuration components of the system 40 such as the switch 52, the security assembly 54, the temperature management assembly 56, and the connectors 44, 46, 48 are positioned on one end of the housing 42, such components may be positioned at any suitable position in the system 40. In some configurations, at least one of the components may be positioned, for example, inside of the housing.

Figure 2C:
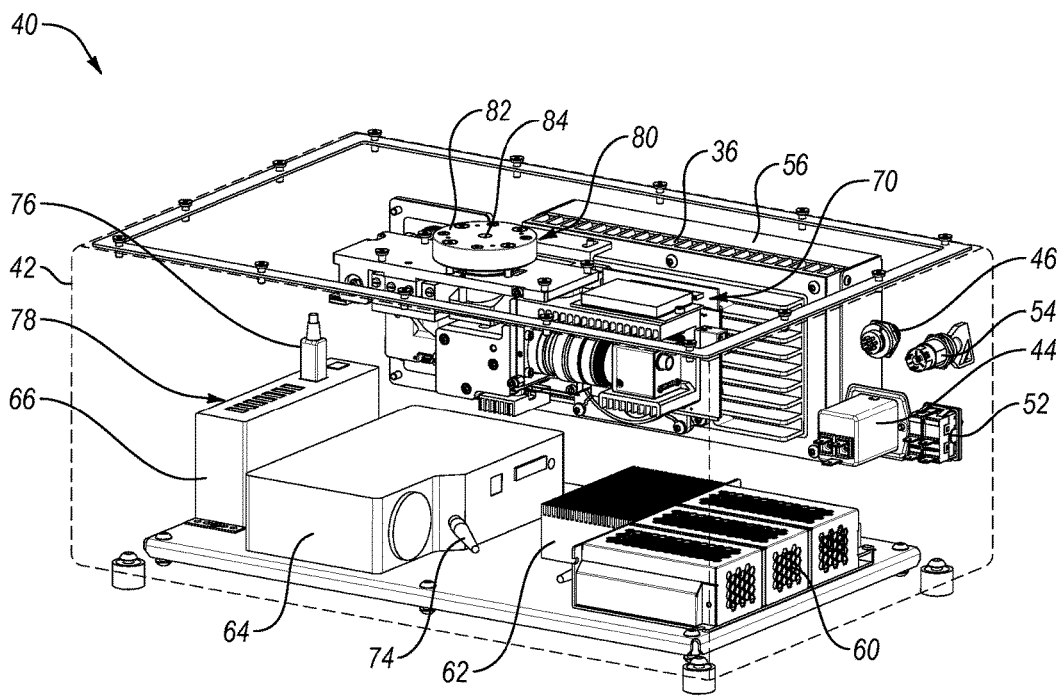
FIGS. 2C-2E are perspective views of a portion of the system of FIG. 2A.
Figure 2D:
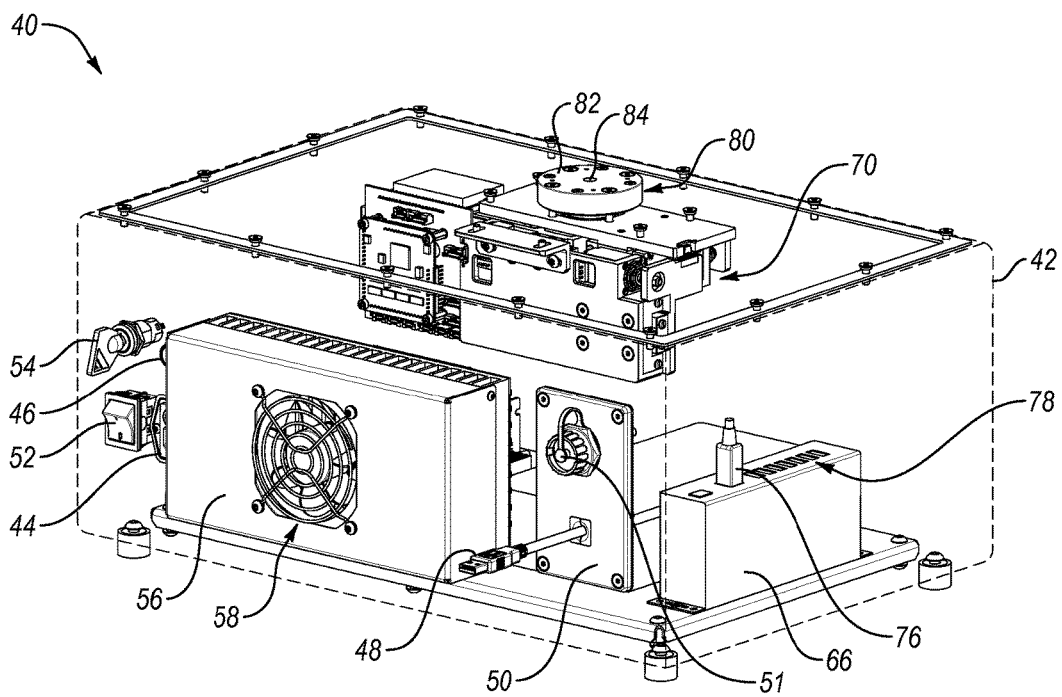
Figure 2E:
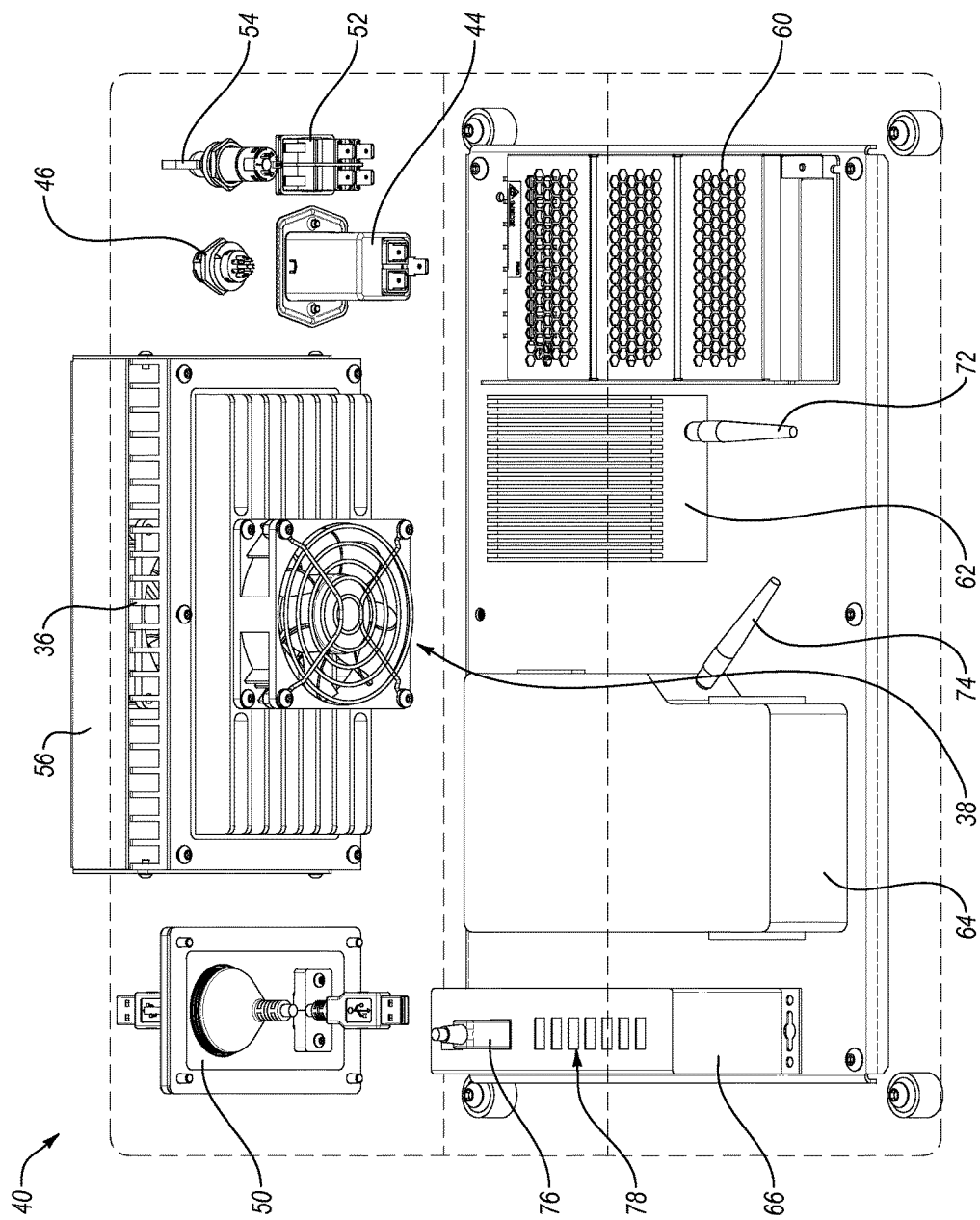

FIGS. 2C, 2D, and 2E illustrate portions of the system 40 inside of the housing 42, which is represented by dashed lines. As illustrated, the system 40 may include a head assembly 70, a power assembly 60, an emitter assembly 62, a detector assembly 64, and an electronic assembly 66 positioned inside of the housing 42. The head assembly 70 may be mechanically coupled to the interface assembly 80 and/or optically coupled to receive and/or transmit electromagnetic radiation to/from the interface assembly 80. The head assembly 70 is omitted from FIG. 2E to illustrate other portions of the system 40.

The power assembly 60 may be configured to control, distribute and/or modulate power supplied to portions of the system 40. In some configurations, the power assembly 60 may be electrically coupled with various portions of the system 40 by electrical couplings such as cables (not illustrated).

The emitter assembly 62 may include an emitter such as the emitter 18 and the detector assembly 64 may include a detector such as detector 20 as described with respect to FIG. 1. The emitter assembly 62 may include a first interface 72 and the detector assembly 64 may include a second interface 74. In some configurations, the first and second interfaces 72, 74 may be optical interfaces configured to optically couple the emitter assembly 62 and/or the detector assembly 64. For example, the first interface 72 may optically couple the emitter assembly 62 to the head assembly 70 via, for example, an optical cable (not illustrated). In another example, the second interface 74 may optically couple the detector assembly 64 to the head assembly 70 via, for example, an optical cable (not illustrated). The emitter assembly 62 may be configured to transmit radiation to the head assembly 70 and/or the detector assembly 64 may be configured to receive radiation from the head assembly 70 to obtain information about samples. In some configurations, the emitter assembly 62 may be a Raman laser source assembly and the detector 20 may be a Raman spectrometer assembly.

In an example implementation, the head assembly 70 may include an objective, an optical multiplexer, a sensor and/or platform such as the objective 12, the optical multiplexer 14, the sensor 16, and/or platform 22 as described with respect to FIG. 1. Additionally or alternatively, the head assembly 70 may include a controller such as controller 28 as described with respect to FIG. 1. The head assembly 70 will be described in further detail below with respect to FIGS. 3A-3F.

The electronic assembly 66 may be configured to distribute data, power and/or control signals to various portions of the system 40. The electronic assembly 66 may include one or more connectors 76, 78 configured to couple various components of the system 40. In some configurations, the electronic assembly 66 may be a USB hub.

Figure 3A:
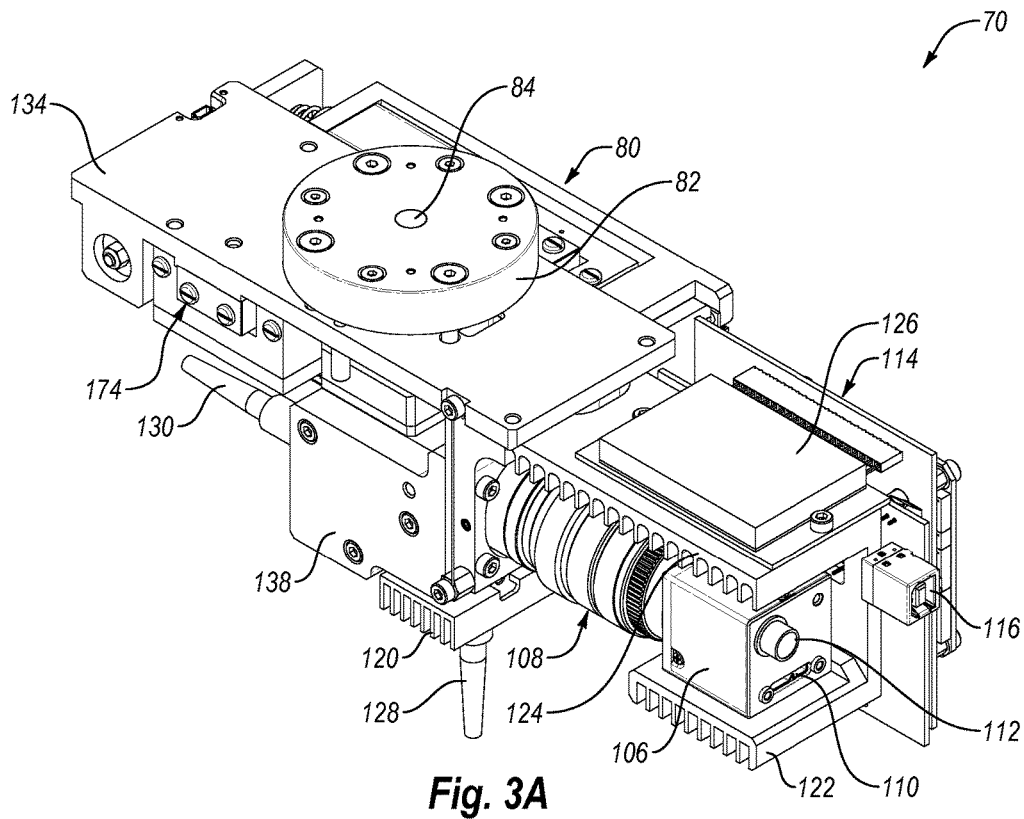
FIGS. 3A-3D are perspective views of a head assembly of the system of FIGS. 2A-2B.
Figure 3B:
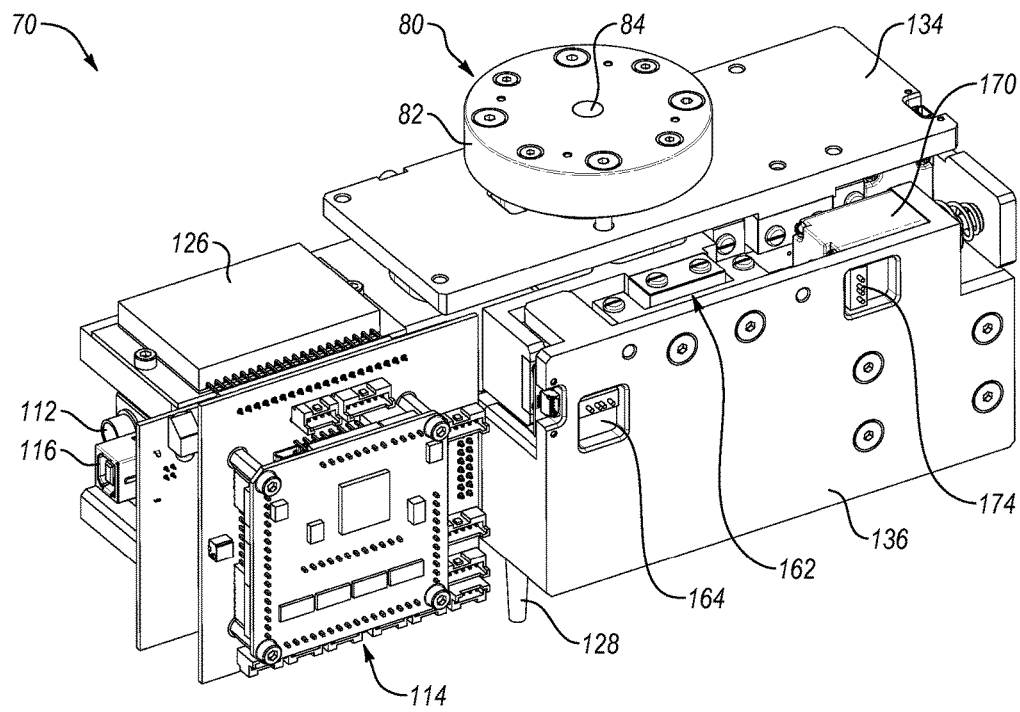
Figure 3C:
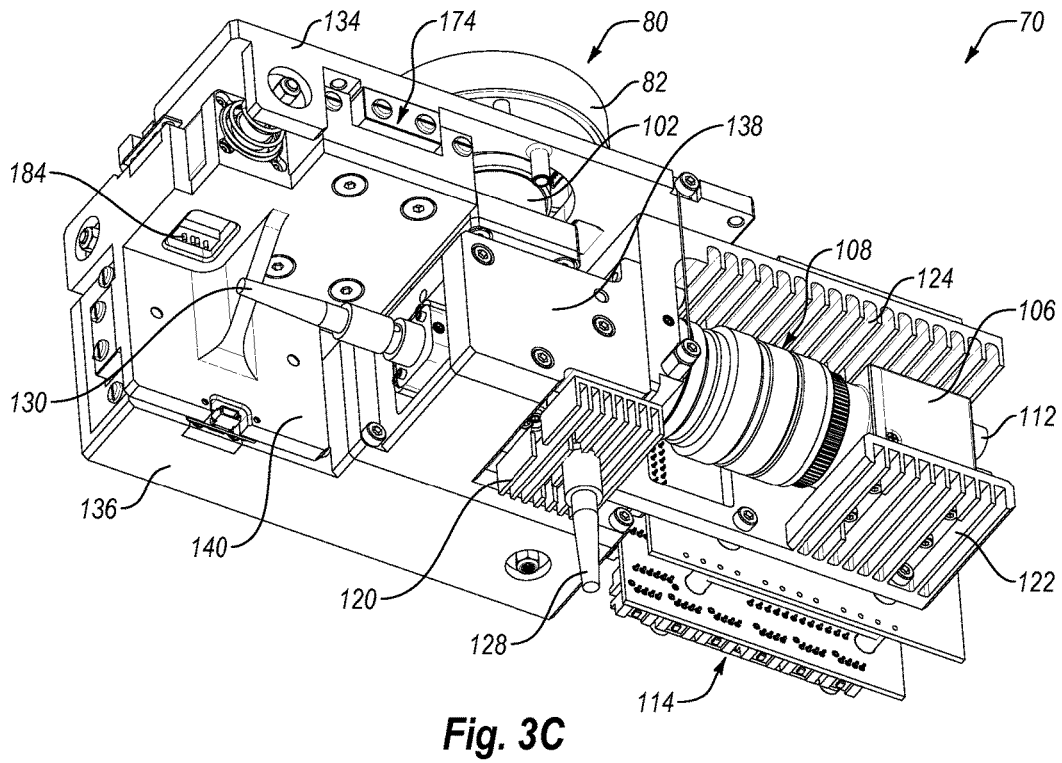
Figure 3D:
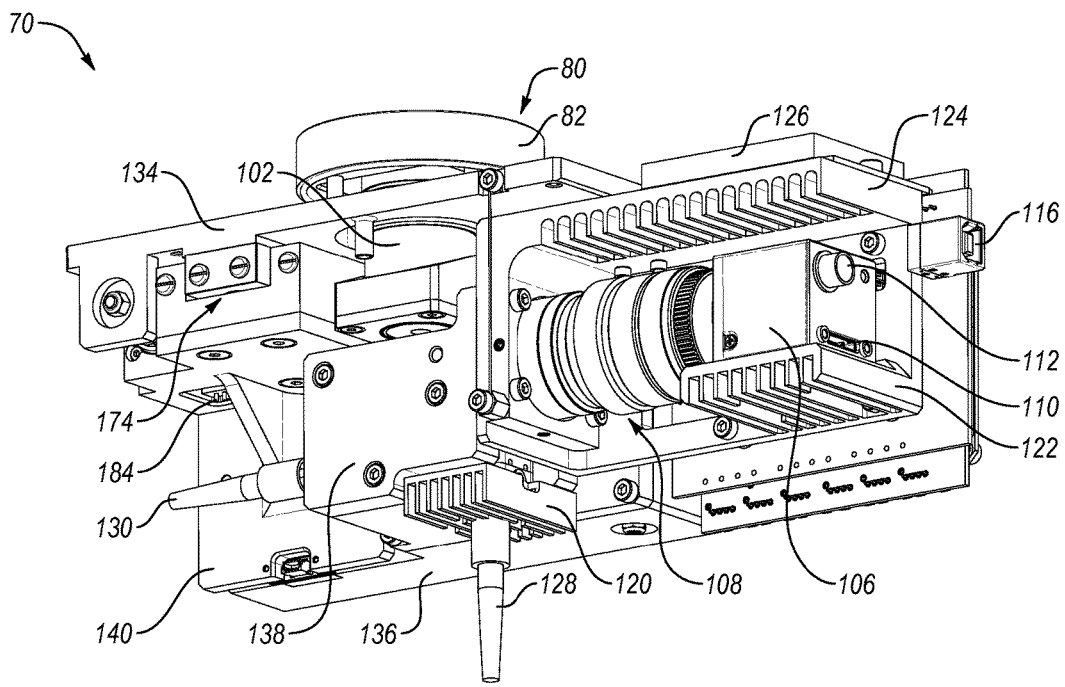
Figure 3E:
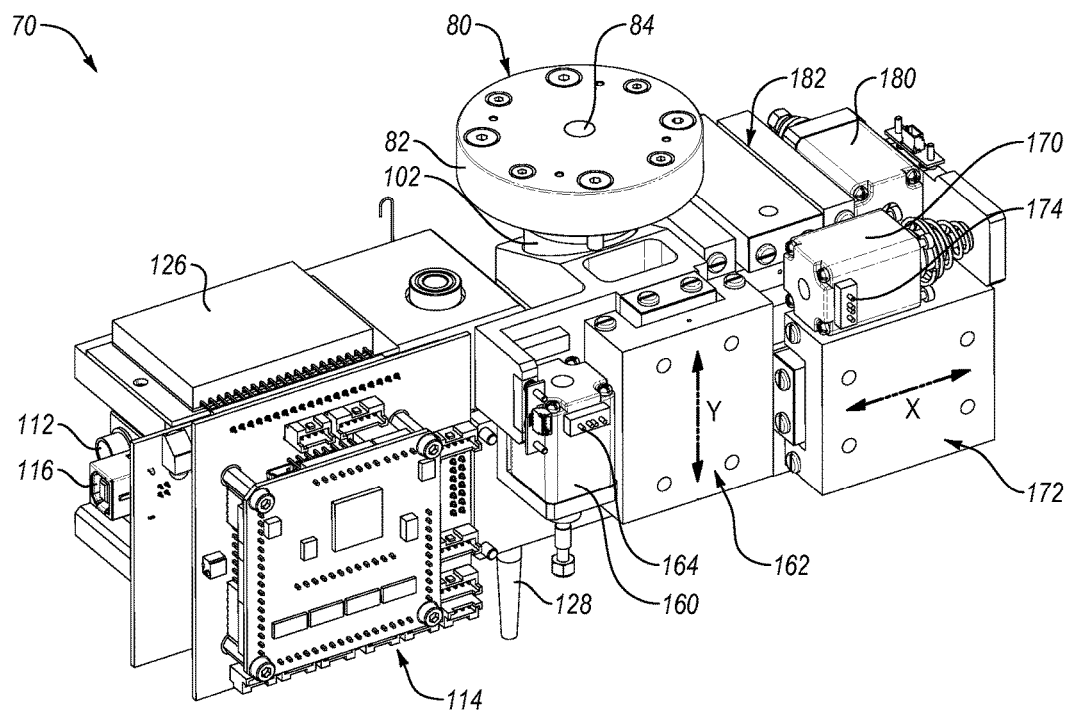
FIGS. 3E-3F are perspective views of a portion of the head assembly of FIGS. 3A-3D.
Figure 3F:
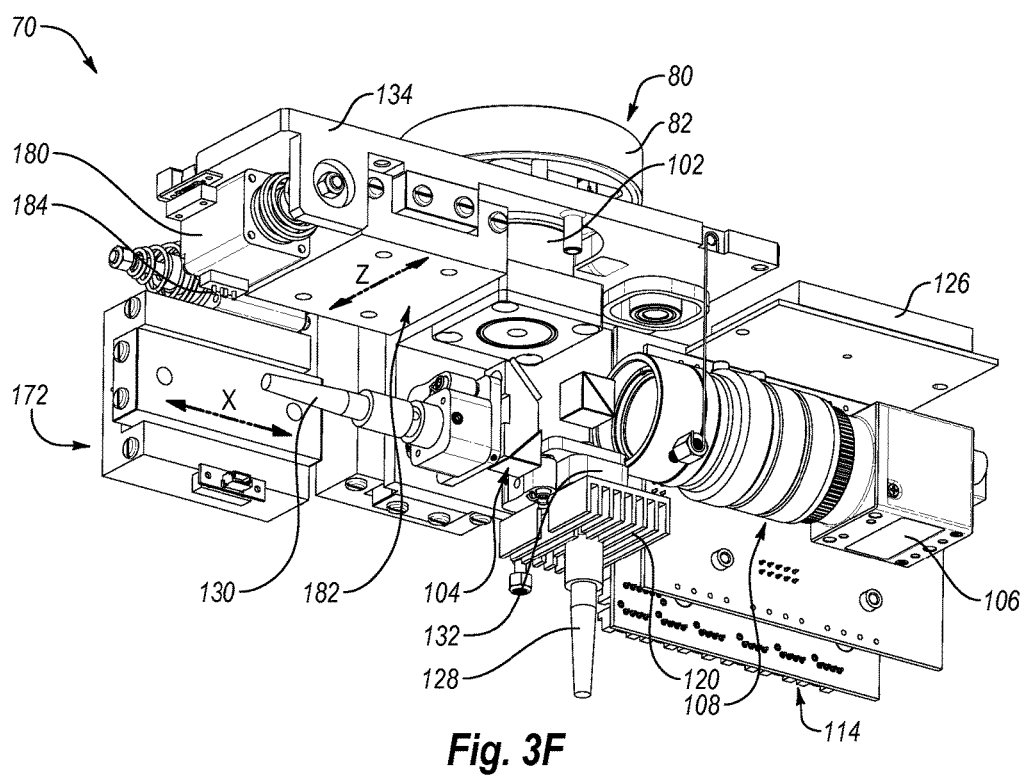

FIGS. 3A-3D illustrate perspective views of an example implementation of the head assembly, denoted generally at 70. FIGS. 3E and 3F illustrate the head assembly 70 with some portions omitted to illustrate other details of the head assembly 70. As illustrated, the head assembly 70 may be optically coupled to receive and/or transmit electromagnetic radiation to/from the interface assembly 80. Specifically, the head assembly 70 may include an objective 102 (see for example FIGS. 3E and 3F) coupled to the interface assembly 80. The objective 102 may include optics configured to convey, direct, collimate and/or focus electromagnetic radiation travelling between the head assembly 70 and the interface assembly 80. As illustrated for example in FIG. 3F, the objective 102 may be optically coupled to an optical multiplexer 104. The optical multiplexer 104 may be configured to distribute electromagnetic radiation travelling through the head assembly 70 and/or other portions of the system 40. Additionally or alternatively, the optical multiplexer 104 may be configured to convey, direct, collimate and/or focus electromagnetic radiation travelling through the head assembly 70 and/or other portions of the system 40.

The head assembly 70 may include a sensor 106 configured to detect characteristics of received electromagnetic radiation such as energy level, wavelength, or other characteristics (for example, as described above with respect to the system 10). The characteristics of the received radiation may be used to determine characteristics of samples. In some configurations, the sensor 106 may be an image sensor (e.g., a color camera, or monochromatic camera) configured to obtain images of samples. An optical assembly 108 may be optically coupled between the optical multiplexer 104 and the sensor 106. The optical assembly 108 may be configured to convey, direct, collimate and/or focus electromagnetic radiation travelling between the optical multiplexer 104 and the sensor 106. The sensor 106 may include a first connector 110 and/or a second connector 112 configured to transmit data, power and/or control signals between the sensor 106 and other portions of the head assembly 70.

The head assembly 70 may be configured such that portions of the head assembly 70 may be moved with respect to the interface assembly 80. For example, in some configurations, the head assembly 70 may move at least the objective 102 with respect to the interface assembly 80. In some configurations, the head assembly 70 may be configured to move portions of the head assembly 70 in three directions of movement (linear, non-linear, angular, etc.), for example, along three axes: X, Y, and Z. In operation, the movement of portions of the head assembly 70 such as the objective 102 may contribute to focusing and/or scanning the samples.

As illustrated for example in FIG. 3E, the head assembly 70 may include one or more motors or actuators 160, 170, 180. Each of the actuators 160, 170, 180 may be coupled to a corresponding slide 162, 172, 172 configured to the permit portions of the head assembly 70 (e.g., the objective 102) to move with respect to the interface assembly 80. In the illustrated configuration, each actuator 160, 170, 180 and slide 162, 172, 172 corresponds to a direction of movement X, Y, and Z. In non-illustrated configurations, the head assembly 70 may include less or more directions of movement, and/or such directions may or may not be orthogonal to one another. Each of the actuators 160, 170, 180 may include a corresponding connector 164, 174, and 184. The connectors 164, 174, 184 may be configured to couple the actuators 160, 170, 180 to other portions of the head assembly 70. The connectors 164, 174, 184 may be electronic connectors configured to transmit data, power and/or control signals. The connectors 164, 174, 184 may transmit power and/or control signals to drive and/or operate the actuators 160, 170, 180 to move portions of the head assembly 70 with respect to the interface assembly 80. The head assembly 70 may include stops corresponding with each of the directions of movement to limit the movement of the portions of the head assembly 70 with respect to the interface assembly 80.

In the illustrated configuration, portions of the head assembly 70 actuate in three linear directions of movement. In other configurations, the head assembly 70 may actuate in any suitable directions of movement, and such directions of movement may not be linear (e.g., rotational, angular, non-linear, etc.). In some configurations, the head assembly 70 may include mirrors that may be rotated and/or actuated to deflect optical beams rather than moving other portions of the head assembly 70.

The head assembly 70 may include an electronic assembly 114 with a controller configured to control the operation of at least a portion of the system 10. The electronic assembly 114 may be configured to distribute power and/or control signals to other components of the head assembly 70. The electronic assembly 114 may be configured to receive data signals from other components of the head assembly 70, such as the sensor 106.

Specifically, the electronic assembly 114 may include one or more connectors 116 configured to couple the electronic assembly 114 to other portions of the head assembly 70. The connector 116 may be electronic connector configured to transmit data, power and/or control signals. The connector 116 may be coupled to other portions of the head assembly 70, such as the sensor 106, the actuators 160, 170, 180 and/or other components. Additionally or alternatively, the connector 116 may be coupled to other portions of the system 40.

The electronic assembly 114 may include a processor that executes instructions stored in memory. As illustrated, the electronic assembly 114 may be incorporated into the head assembly 70. In other configurations, the electronic assembly 114 may be a separate component external to the head assembly 70. For example, the head assembly 70 may be controlled and/or operated by a computer system coupled to the head assembly 70. The electronic assembly 114 can include executable instructions that control the operation of the head assembly 70. For example, the electronic assembly 114 can include instructions that when executed cause the head assembly 70 to analyze and/or scan one or more samples.

The head assembly 70 may include an electronic assembly 126, which in some configurations may be a temperature management assembly configured to manage the temperature of portions of the head assembly 70. For example, the electronic assembly 126 may be configured to cool portions of the head assembly 70. The electronic assembly 126 may include a Peltier device, Peltier heat pump, solid state refrigerator, and/or a thermoelectric cooler. The electronic assembly 126 may include a controller configured to manage the temperature of portions of the head assembly 70 by controlling the operation of a Peltier device, Peltier heat pump, solid state refrigerator, and/or a thermoelectric cooler.

As illustrated for example in FIG. 3F, the head assembly 70 may include an emitter 132 configured to emit radiation to analyze samples. The emitter 132 may emit any suitable electromagnetic radiation to analyze and/or process samples. For example, the emitter 132 may emit visible light, ultraviolet light, X-rays, infrared or any other suitable radiation. In some configurations, the emitter 132 may be a laser or diode. In some configurations, the emitter 132 may be a Raman laser source. The emitter 132 may be optically coupled with the optical multiplexer 104. In such configurations, the optical multiplexer 104 may be configured to convey, direct, collimate and/or focus electromagnetic radiation from the emitter 132. For example, the optical multiplexer 104 may be configured to direct radiation from the emitter 132 to a sample.

In addition to or as an alternative to the emitter 132, the head assembly 70 may include an optical interface 128 configured to optically couple the head assembly 70 to other components of the system 40. For example, the optical interface 128 may couple the head assembly 70 to an emitter, such as the emitter assembly 62 as described above with respect to FIGS. 2C and 2E. The optical interface 128 may optically couple the head assembly 70 to the emitter assembly 62 via, for example, an optical cable (not illustrated). The emitter assembly 62 may be configured to transmit electromagnetic radiation to the head assembly 70. In such configurations, the optical multiplexer 104 may be configured to convey, direct, collimate and/or focus electromagnetic radiation from the emitter assembly 62. For example, the optical multiplexer 104 may be configured to direct radiation from the emitter assembly 62 to a sample.

The head assembly 70 may include a second optical interface 130 configured to optically couple the head assembly 70 to other components of the system 40. For example, the optical interface 130 may couple the head assembly 70 to a detector, such as the detector assembly 64 as illustrated and described with respect to FIGS. 2C and 2E, for example. The optical interface 130 may optically couple the head assembly 70 to the detector assembly 64 via, for example, an optical cable (not illustrated). The detector assembly 64 may be configured to receive radiation from the head assembly 70 to obtain information about samples. In such configurations, the optical multiplexer 104 may be configured to convey, direct, collimate and/or focus electromagnetic radiation to the detector assembly 64. For example, the optical multiplexer 104 may be configured to distribute radiation from samples to the detector assembly 64.

The head assembly 70 may include one or more support members 134, 136, 138, 140 configured to support, enclose, and/or couple portions of the head assembly 70 to one another. The configuration of the support members 134, 136, 138, 140 may permit portions of the head assembly 70 to move in the X, Y, and Z directions. Additionally or alternatively, the configuration of the support members 134, 136, 138, 140 may limit the range of motion of portions of the head assembly 70 in the X, Y, and Z directions.

The head assembly 70 may include one or more heat sinks 120, 122, 124 configured to facilitate cooling of portions of the head assembly 70. In some configurations, the heat sinks 120, 122, 124 may be configured to cool specific components of the head assembly 70. For example, in the illustrated configuration, the heat sink 120 is configured to cool the emitter 132, the heat sink 122 is configured to cool the sensor 106 and the heat sink 124 is configured to cool the electronic assembly 126 or other portions of the head assembly 70. In other configurations, the head assembly 70 may include more or less heat sinks; the heat sinks 120, 122, 124 may be configured in other manners; or may be omitted entirely. Additionally or alternatively, the temperature of the components of the head assembly 70 may be managed by other temperature control systems and/or mechanisms.

In some configurations, the head assembly 70 may include any suitable aspects as described with respect to the system 10 of FIG. 1.

Figure 4A:
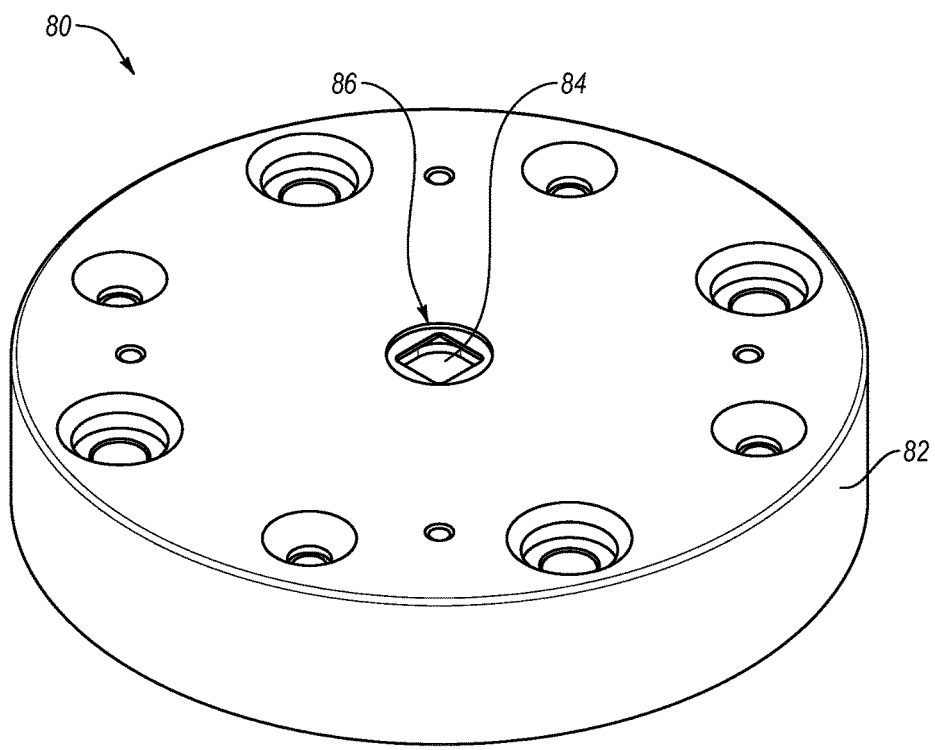
FIGS. 4A-4B are perspective views of an interface assembly of the system of FIGS. 2A-2B.
Figure 4B:
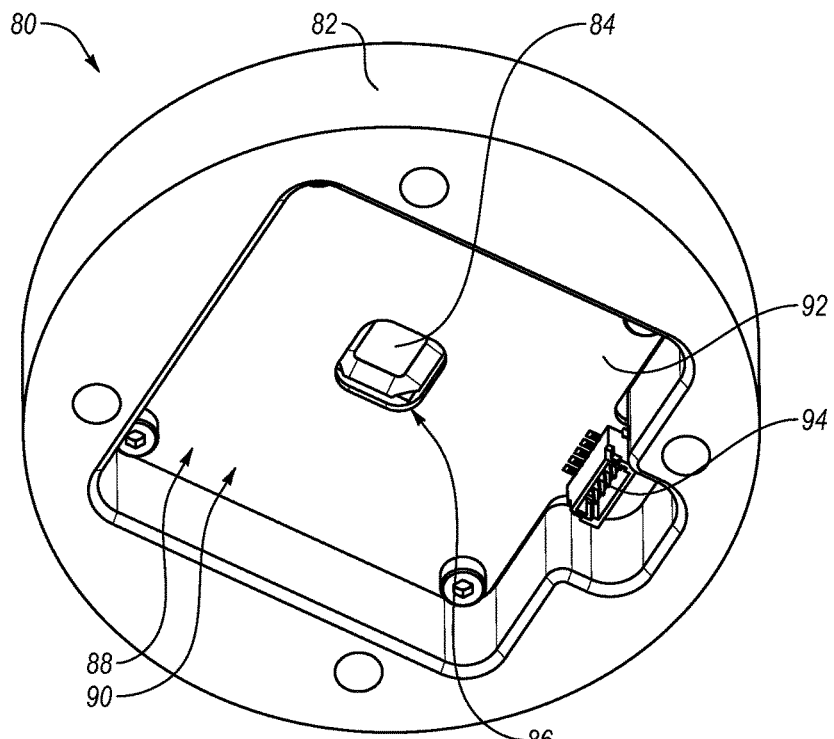

FIGS. 4A and 4B illustrate one example embodiment of the interface assembly, denoted generally at 80, in further detail. The interface assembly 80 may be configured to interface with other portions of the system 40, such as the head assembly 70 and/or other components of the system 40 that will be described in further detail below. As illustrated, the body 82 of the interface assembly 80 defines an aperture 86 extending at least partially through the interface assembly 80. The aperture 86 may be configured (e.g. shaped and/or dimensioned) to permit electromagnetic radiation to travel through at least a portion of the interface assembly 80 to the window 84. The window 84 may be at least partially transparent or translucent and/or may be configured to convey, direct, collimate and/or focus light travelling through the interface assembly 80.

As illustrated for example in FIG. 4B, the body 82 of the interface assembly 80 may define a receptacle 88 with an optoelectronic assembly 90 positioned therein. The optoelectronic assembly 90 will be described in further detail below with respect to FIGS. 5A-5B. The optoelectronic assembly 90 may be removably or non-removably fastened to the body 82 of the interface assembly 80 inside of the receptacle 88. The optoelectronic assembly 90 may include a body 92 and a connector 94 coupled to the body 92. In some configurations, the body 92 may be an electronic board such as a printed circuit board (PCB). The connector 94 may be configured to couple the optoelectronic assembly 90 to other portions of the system 40. The body 92 may include an opening further defining the aperture 86 of the interface assembly 80.

Figure 5A:
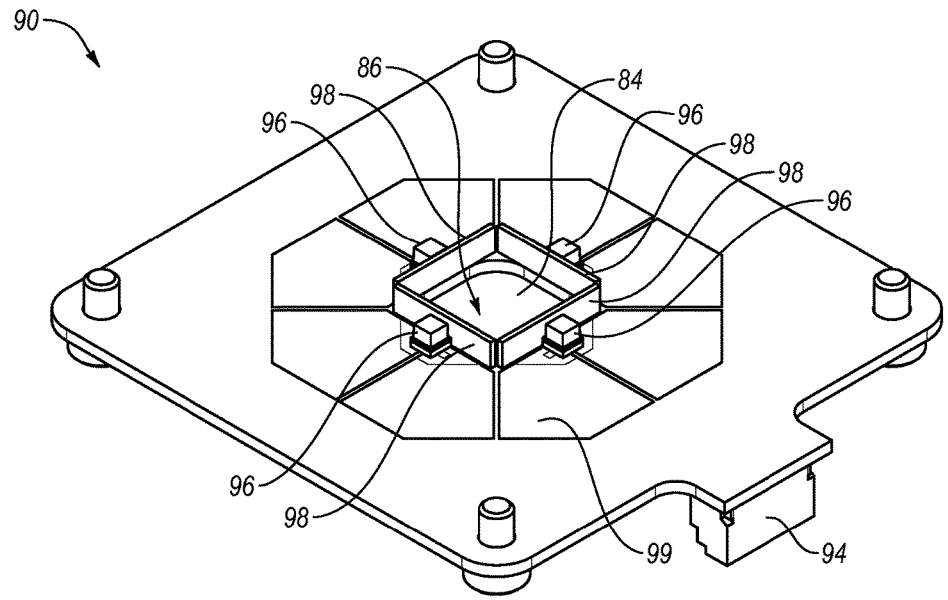
FIGS. 5A-5B are perspective views of a portion of the interface assembly of FIGS. 4A-4B.
Figure 5B:
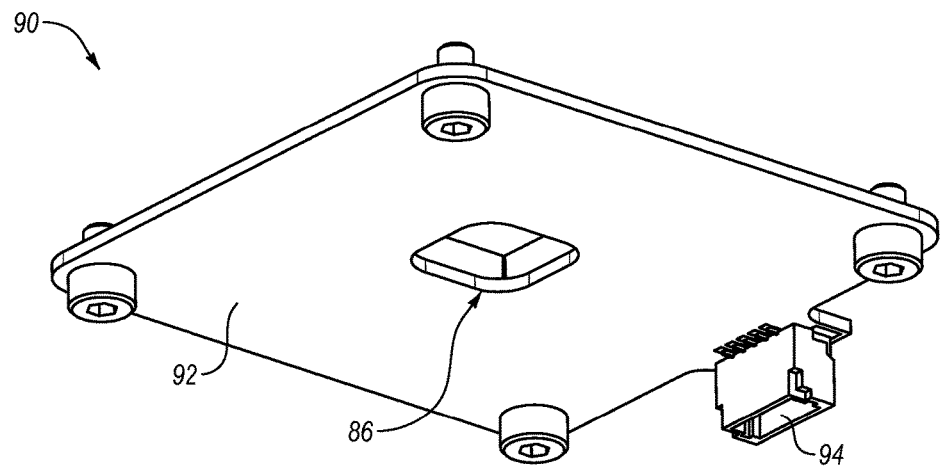

Turning to FIGS. 5A and 5B, the optoelectronic assembly 90 will be described in further detail. As illustrated, the optoelectronic assembly 90 may include one or more emitters 96 positioned around the aperture 86. One or more polarizers 98 may be positioned between each of the emitter 96 and the aperture 86. The emitters 96 may be configured to emit visible light, ultraviolet light, X-rays, infrared or any other suitable radiation. The emitter 96 may be any suitable electromagnetic radiation source. In some configurations, the emitter 96 may be a laser or a diode. In some configurations, the optoelectronic assembly 90 may include multiple emitters 96 and one or more of the emitters 96 may be configured to output electromagnetic radiation of different characteristics from one another. The emitters 96 may be electrically coupled to the connector 94 by any suitable electrical coupling. For example, the emitters 96 may be electrically coupled to the connector 94 by conductive traces printed on the body 92 or running through the body 92. The connector 94 may be coupled to other portions of the system 40. The connector 94 may permit power and/or control signals to be transmitted to the emitters 96. The connector 94 may also permit feedback and/or data to be transmitted from the optoelectronic assembly 90 to other portions of the system 40.

As illustrated for example in FIG. 5A, a heat conductive material 99 may be coupled to the body 92. The heat conductive material 99 may be configured to facilitate managing the temperature of the optoelectronic assembly 90 and/or the interface assembly 80. For example, the heat conductive material 99 may permit heat to be dissipated from portions of the optoelectronic assembly 90 and/or the interface assembly 80. Specifically, heat generated during operation of the emitters 96 may be conducted through the heat conductive material 99 and may dissipate away from the emitters 96. Additionally or alternatively, the heat conductive material 99 may dissipate heat from the polarizers 98 and/or other portions of the interface assembly 80. In some configurations, the heat conductive material 99 may be copper or may at least partially include copper.

Figure 5C:
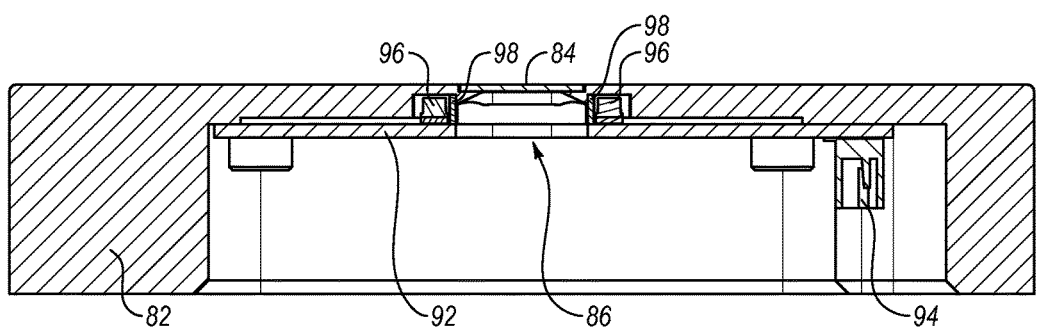
FIG. 5C is a cross-sectional view of the interface assembly of FIGS. 4A-4B.

FIG. 5C illustrates a cross-sectional view of the interface assembly 80 with the optoelectronic assembly 90. In operation, a sample may be positioned over the window 84 and the head assembly 70 may be activated to analyze and/or process the sample. In some configurations, the window 84 may be sealed to the body 82 such that substances may not travel between the window 84 and the body 82 at their interface. For example, the interface assembly 80 may include a seal such as an O-ring between the window 84 and the body 82. The window 84 and/or the aperture 86 may permit light to travel through the interface assembly 80, for example, between the sample and the objective 102 of the head assembly 70. The optoelectronic assembly 90 may be coupled to the body 82 such that the objective 102 of the head assembly 70 is a specified distance or range of distances from the optoelectronic assembly 90.

Figure 6A:
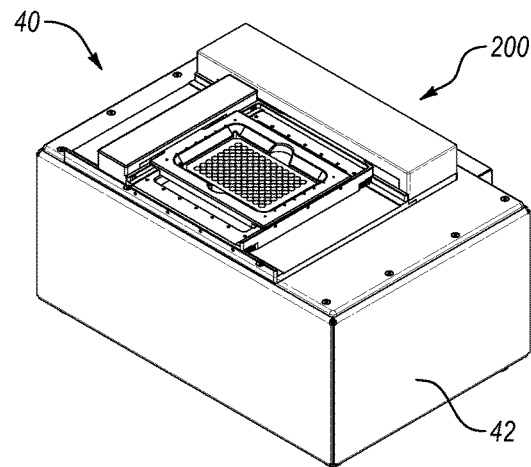
FIG. 6A is a perspective view of a non-limiting embodiment of the system of FIGS. 2A-2B with a device configured to analyze one or more samples positioned in a sample tray.
Figure 6B:
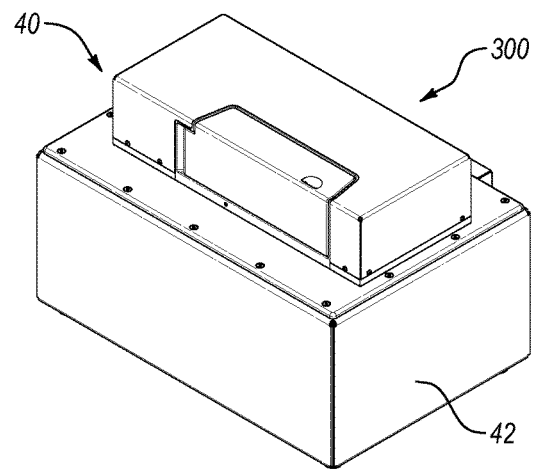
FIG. 6B is a perspective view of a non-limiting embodiment of the system of FIGS. 2A-2B with a device configured to analyze layers of samples.
Figure 6C:
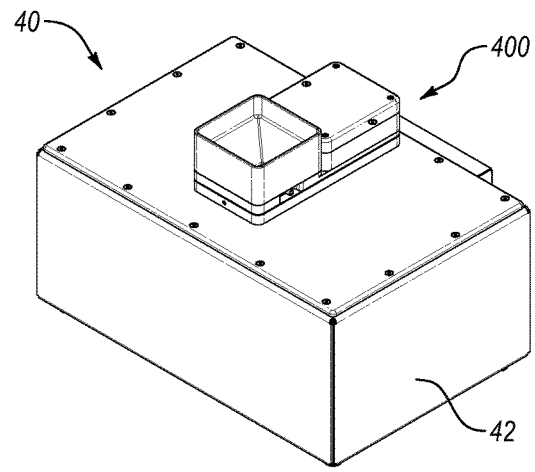
FIG. 6C is a perspective view of a non-limiting embodiment of the system of FIGS. 2A-2B with a device configured to analyze granular samples.

FIGS. 6A-6C illustrate the system 40 with different example configurations to process samples of different types and/or by different methods or techniques. FIG. 6A illustrates the system 40 with a device 200 configured to analyze one or more samples positioned in a sample tray. FIG. 6B illustrates the system 40 with a device 300 configured to analyze layers of samples, for example pills, tablets, capsules, medication, pellets, and/or other substances. FIG. 6C illustrates the system 40 with a device 400 configured to analyze particle samples such as powders, granules, and/or other substances. The system 40 may also be configured to analyze fluid samples such as liquids, gels, gases, and/or other substances. In such configurations, the system 40 may include an interface assembly 80 adapted to receive, deliver, process and/or analyze liquids, gels, gases, and/or other substances.

As mentioned above, the system 40 may be modular to permit the system 40 to be configured to analyze or process different types of samples. Additionally or alternatively, the system 40 may be modular to permit the system 40 to be configured to analyze or process samples by one or more different methods or techniques. Specifically, the interface assembly 80 may interface with modular components and/or devices. The modular components and/or devices may be configured to process, prepare and/or deliver analytes or samples over the window 84 to be analyzed by the system 40. The modular components and/or devices may include configurations suited for processing a specific type of sample or analyzing samples by a specific method or process. Additionally or alternatively, the modular components and/or devices may be configured to process samples either before or after they are analyzed, or both. For example, the modular components and/or devices may prepare the samples to be analyzed by the system 40. In another example, the modular components and/or devices may sort and/or separate samples after the samples are analyzed, for example, based on information obtained when the samples were analyzed.

Figure 7A:
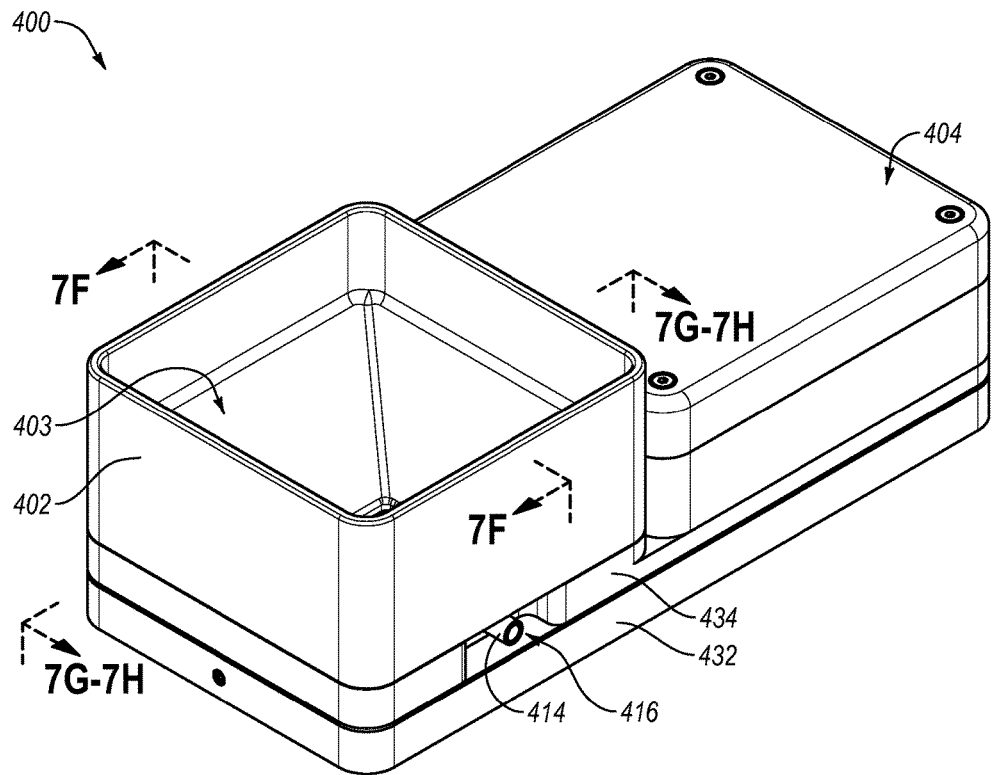
FIGS. 7A-7B are perspective views of the non-limiting embodiment of the device configured to analyze granular samples of FIG. 6C.
Figure 7B:
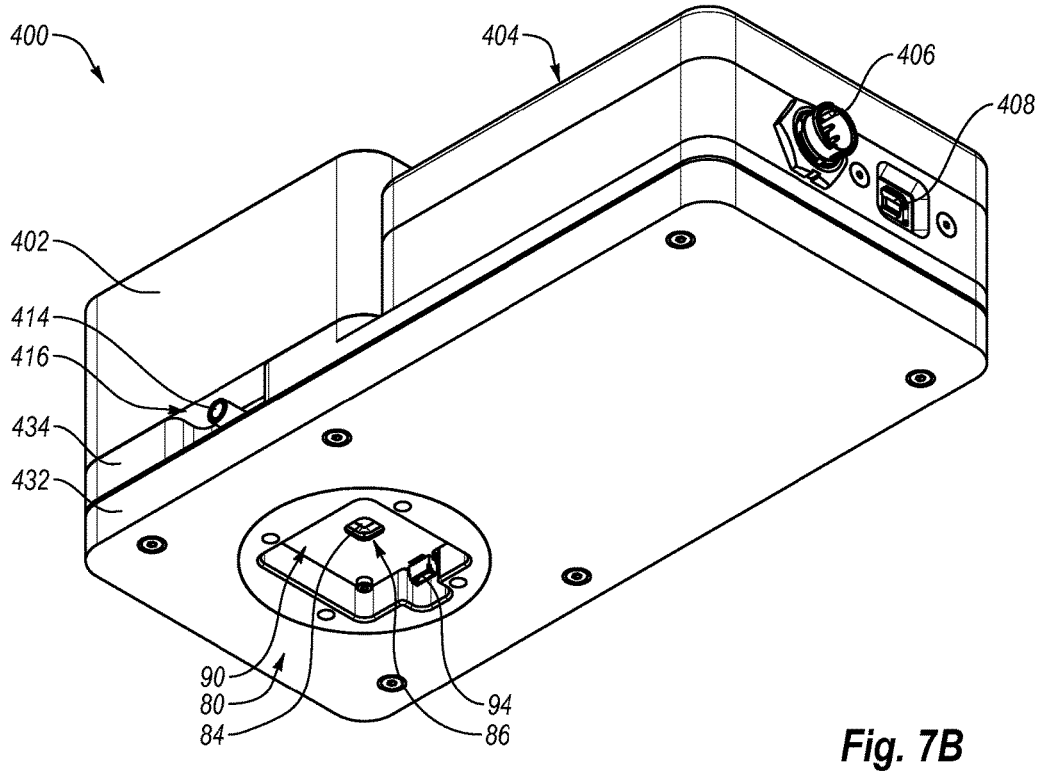

Turning to FIGS. 7A-7H, one example embodiment of the device 400 will be described in further detail. FIGS. 7A and 7B are perspective views of the device 400. As illustrated, the device 400 may include a first body portion 432 and a second body portion 434 coupled to one another. The device 400 may include a sample feeder such as a hopper 402 configured to receive a substance to be analyzed by the system 40. A housing 404 surrounding at least a portion of the device 400 may be positioned over and/or coupled to the body portion 434 adjacent to the hopper 402.

As illustrated, the hopper 402 may be positioned over and/or coupled to the body portion 434. The hopper 402 may feed substances into the device 400 to be analyzed and/or processed by the system 40. The hopper 402 may be configured to retain substances before they are analyzed and/or processed. Specifically, the hopper 402 may define a receptacle 403 configured to retain substances and/or feed substances into the device 400. The substances may be particle samples such as powders, granules, particulates, fragments, portions and/or other substances. In some configurations, the substances may be granular samples and/or pharmaceutical micro-structured blends of substances.

In other configurations, the device 400 may include other suitable sample feeders instead of the hopper 402. For example, the sample feeder may be a receptacle or compartment configured to retain substances. In some configurations, the sample feeder may be a conduit permitting substances to be analyzed from a production process. The sample feeder may be a continuous or semi-continuous feed of substance. For example, the sample feeder may be a conduit permitting substances in a production process to be continuously or semi-continuously analyzed by the system 40.

FIG. 7B illustrates the device 400 including the interface assembly 80 of the system 40. As illustrated, the device 400 may include a first connector 406, and a second connector 408 connecting portions of the device 400 inside of the housing 404 to other portions of the system 40. The connectors 406 and 408 may be electronic connectors configured to transmit data, power and/or control signals. In some configurations, the connector 406 may be coupled to corresponding connector 46 of the system 40 and/or the connector 408 may be coupled to corresponding connector 48 of the system 40.

The device 400 may be coupled to the interface assembly 80 to permit substances to be analyzed and/or processed by the head assembly 70 via the interface assembly 80. In some configurations, the device 400 may be positioned over the housing 42 of the system 40 and coupled to the system 40 via the interface assembly 80. As illustrated for example in FIG. 7B, the interface assembly 80 may be positioned in a receptacle defined by the body portion 432. The receptacle may be sized and/or shaped to receive the interface assembly 80. When the device 400 is positioned around the interface assembly 80, it may be supported by the housing 42 (see for example, FIG. 6C). The interface assembly 80 may be removably or non-removably coupled to the device 400 by any suitable fasteners, couplings, and/or adhesives. In other configurations, the interface assembly 80 may be integrally formed with the device 400. For example, the interface assembly 80 may be integrally formed as part of the body portion 432.

Figure 7C:
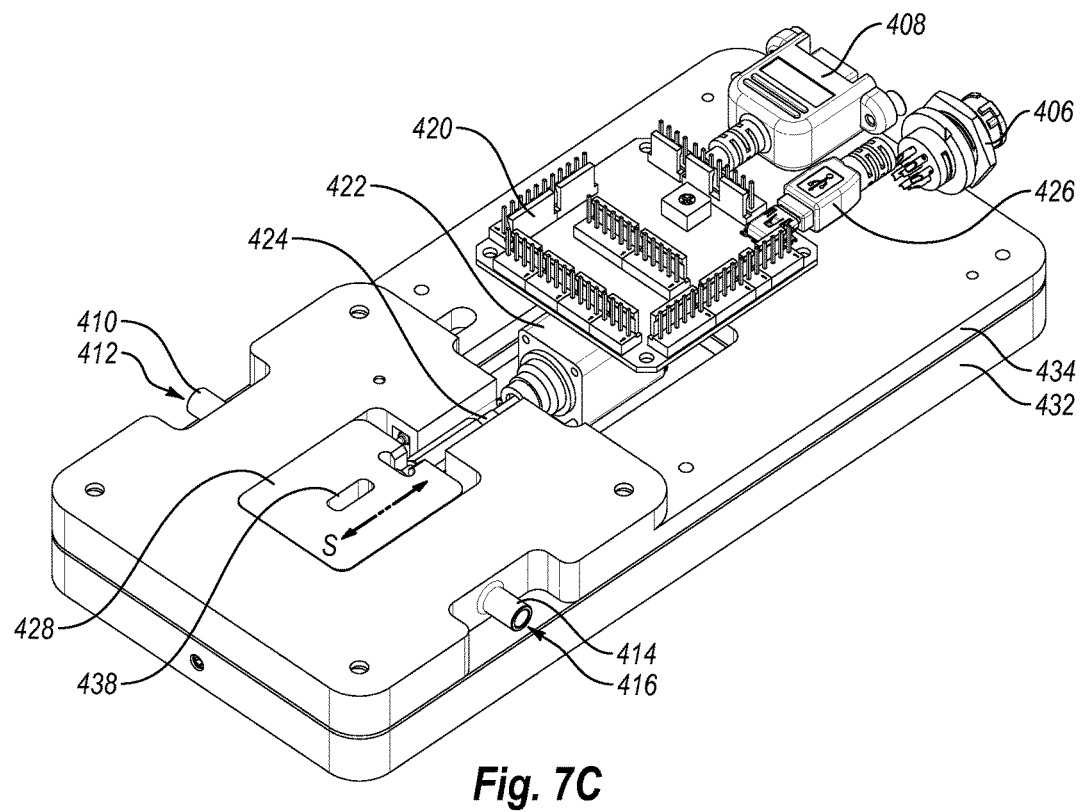
FIGS. 7C-7D are perspective views of a portion of the device of FIGS. 7A-7B.

FIG. 7C illustrates the device 400 with the hopper 402 and the housing 404 not shown. As illustrated, the device 400 may include an inlet 410 and an outlet 414 which may be positioned on the body portion 434. The body portion 434 may define an outlet conduit 416 configured to permit gaseous or liquid fluid to exit the device 400. Additionally or alternatively, the body portion 434 may define an inlet conduit 412 configured to permit gaseous or liquid fluid to enter the device 400. In some circumstances, the gaseous or liquid fluid may include solid substances and/or particles. For example, fluid exiting the device 400 via the outlet conduit 416 may include solid substances after they have been analyzed and/or processed by the system 40 including the device 400.

Figure 7D:
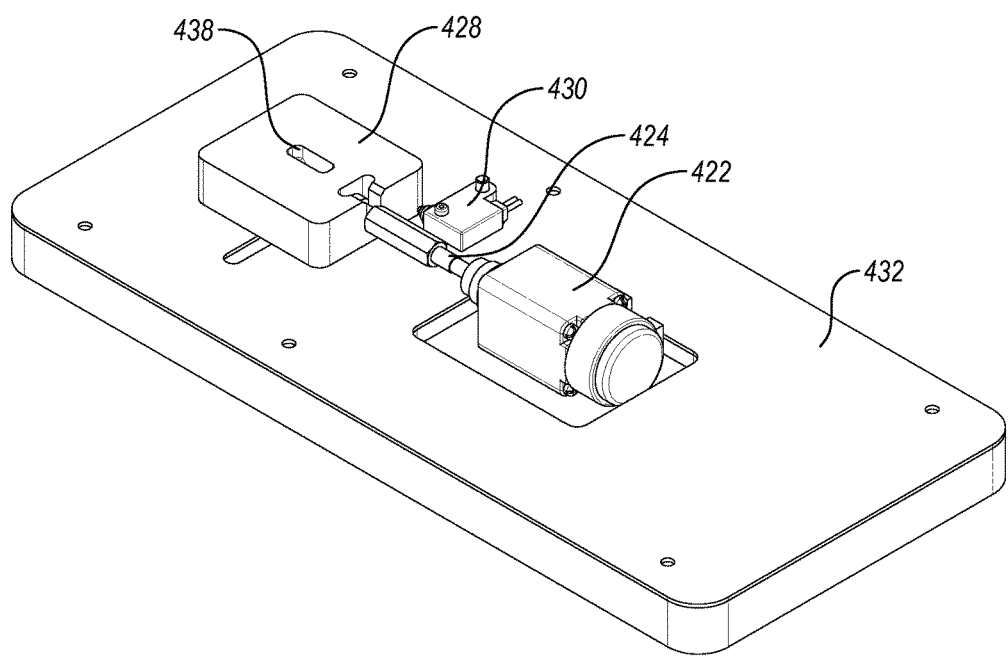
Figure 7E:
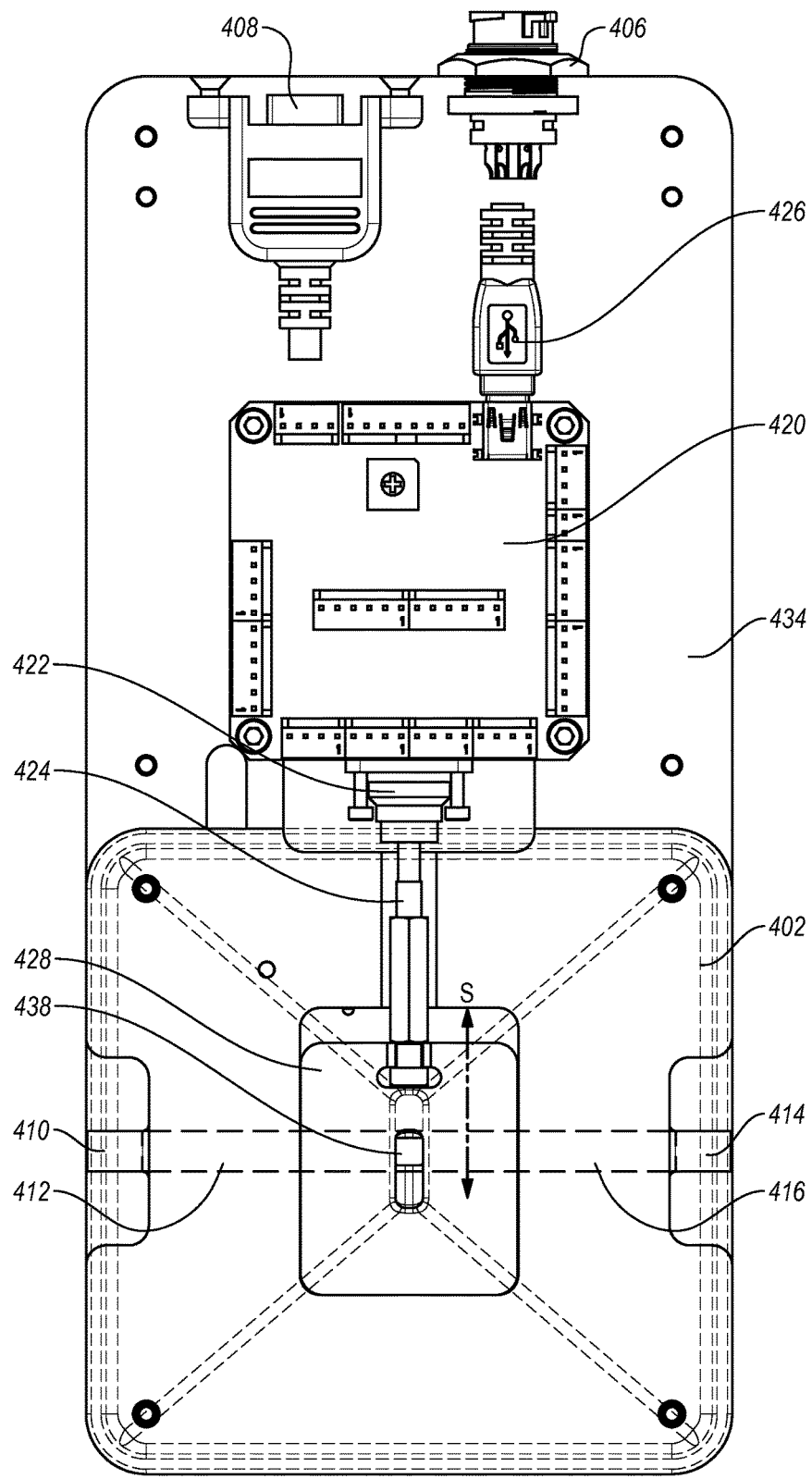
FIG. 7E is a top view of a portion of the device of FIGS. 7A-7B.

FIG. 7D is a perspective view of the device 400 with portions not shown to illustrate aspects of the device 400. FIG. 7E illustrates a top view of the device 400 with the housing 404 not shown and the hopper 402, the inlet conduit 412, and the outlet conduit 416 represented with dashed lines. As illustrated for example in FIGS. 7D and 7E, the device 400 may include one or more motors or actuators 422. In some configurations, for example if the actuator 422 is a rotational motor, the actuator 422 may be coupled to a corresponding transmission member 424 such as a lead screw configured to translate rotational motion to linear motion. In other configurations, the actuator 422 may be a linear actuator configured to convey linear motion, and the transmission member 424 may be a shaft, coupling member, and/or omitted altogether. As illustrated, the transmission member 424 may be coupled to a shuttle 428 such that the actuator 422 may drive the shuttle 428 along the direction of movement S.

The device 400 may include an electronic assembly 420 with one or more connectors 426. The connector 426 may be an electronic connector configured to transmit data, power, feedback and/or control signals. In some configurations, the connector 426 may be coupled to other portions of the device 400 and/or to other portions of the system 40. The electronic assembly 420 may include cables electrically coupled to corresponding connectors of the actuator 422 (not illustrated).

The electronic assembly 420 may include a controller configured to control the operation of at least a portion of the device 400. The electronic assembly 420 may be configured to distribute power and/or control signals to other components of the device 400, such as the actuator 422. The electronic assembly 420 may be configured to receive data signals and/or feedback from the actuator 422. The electronic assembly 420 may be configured to receive power and/or control signals from other portions of the system 40, and/or may distribute such power and/or control signals to portions of the device 400, such as the actuator 422. In some configurations, the electronic assembly 420 may include any suitable aspects described with respect to the controller 28.

The electronic assembly 420 may include a processor that executes instructions stored in memory. As illustrated, the electronic assembly 420 may be incorporated into the device 400. In other configurations, the electronic assembly 420 may be positioned as a separate component external to the device 400. For example, the device 400 may be controlled and/or operated by a computer system coupled to the device 400. The electronic assembly 420 can include executable instructions that control the operation of the device 400. For example, the electronic assembly 420 can include instructions that when executed cause the device 400 to move the shuttle 428 to analyze and/or scan substances positioned in the hopper 402.

The electronic assembly 420 and/or the actuator 422 may be at least partially enclosed by the housing 404 with connectors configured to transmit data, power and/or control signals between the electronic assembly 420, the actuator 422 and/or other portions of the system 40.

Figure 7F:
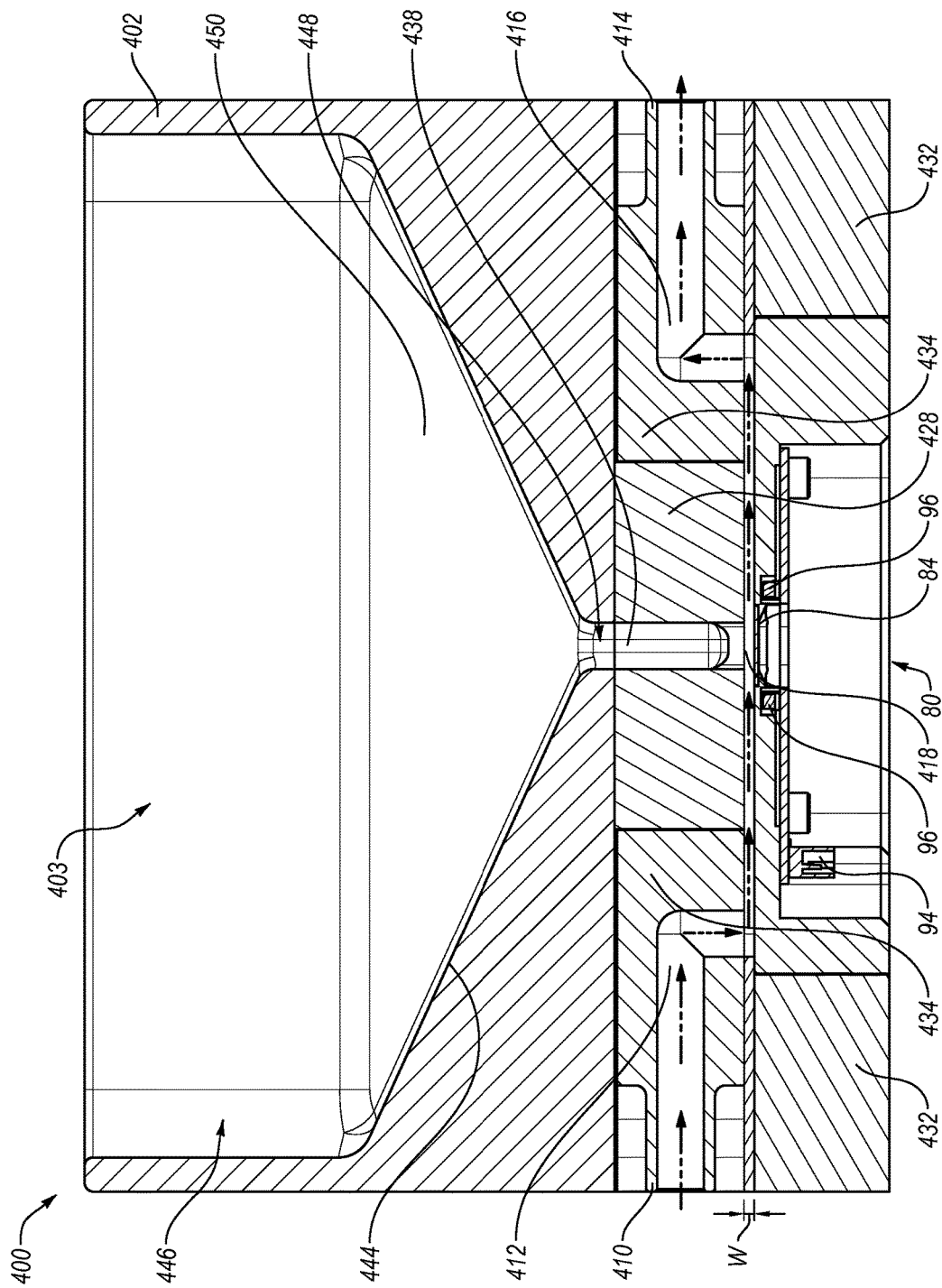
FIG. 7F is a cross-sectional view of the device taken along view line 7F-7F of FIG. 7A.
Figure 7G:
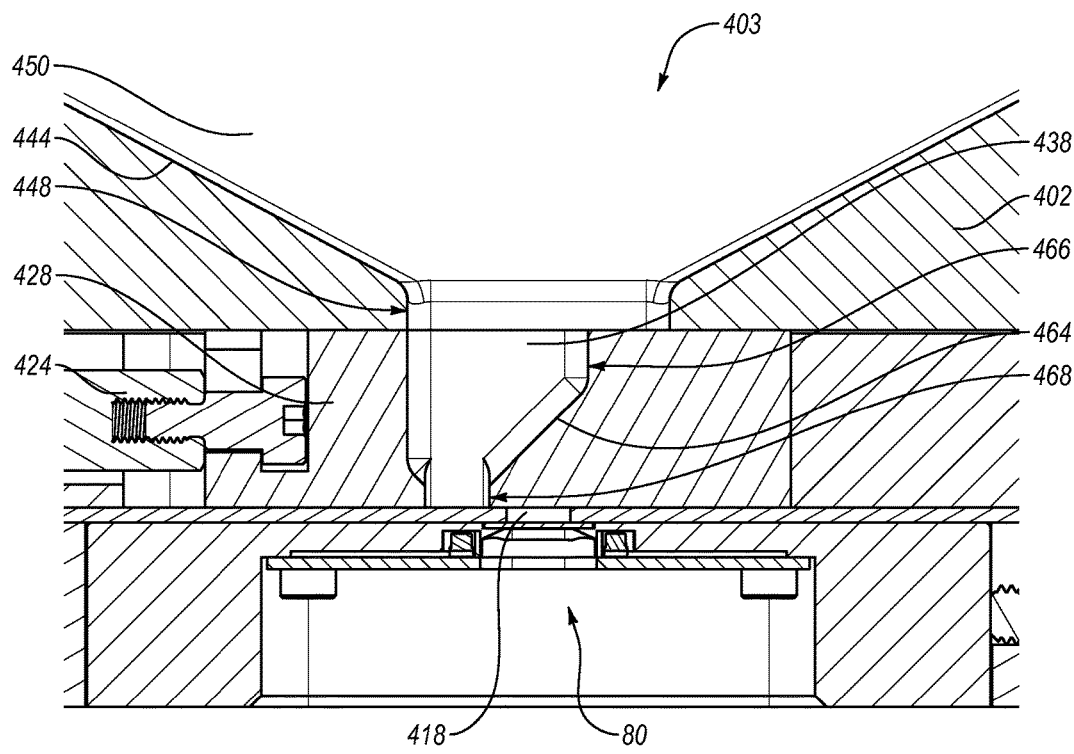
FIGS. 7G and 7H are cross sectional views of the device taken along view line 7GH-7GH of FIG. 7A.
Figure 7H:
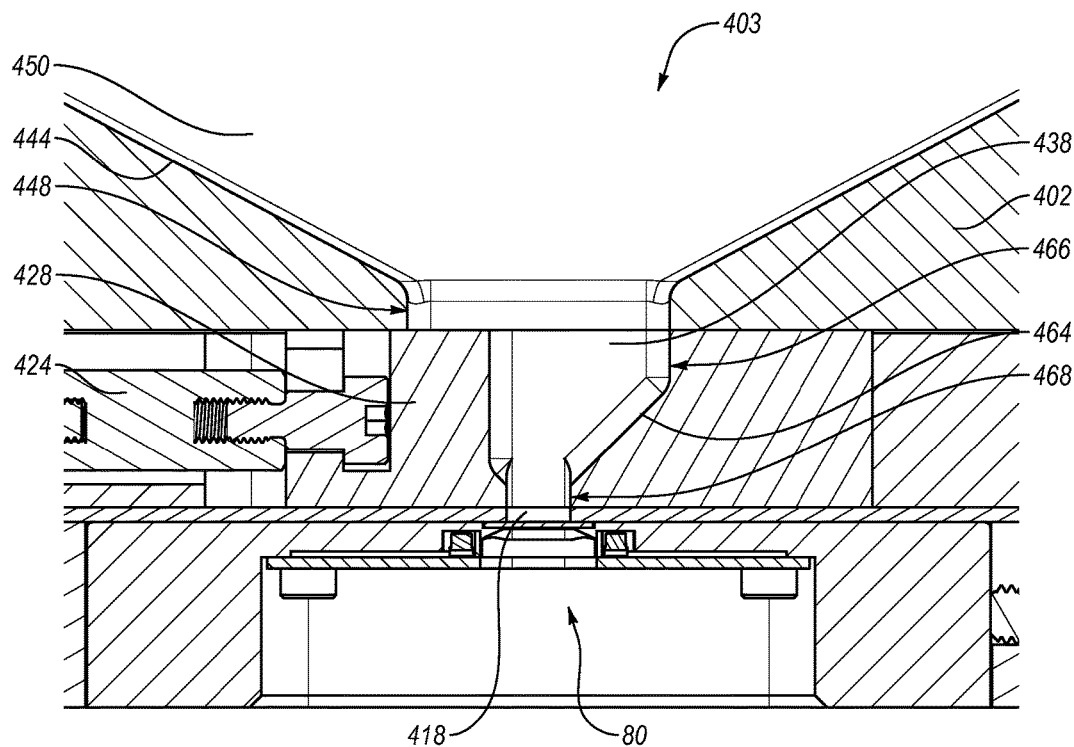

FIGS. 7F-7H are cross-sectional views of the device 400 coupled to the interface assembly 80 and including a substance 450 positioned in the receptacle 403 of the hopper 402. The substance 450 may be particle samples such as powders, granules, particulates, fragments, portions and/or other substances. In some configurations, the substance 450 may be granular samples and/or pharmaceutical microstructured blends of substances.

As illustrated for example in FIG. 7F, the inlet conduit 412 may extend through the body portion 434 and fluidly couple a sample chamber 418 defined between the interface assembly 80 and the device 400. The outlet conduit 416 may extend through the body portion 434 and fluidly couple the chamber 418. The inlet conduit 412 may permit gaseous or liquid fluid to enter the chamber 418 and the outlet conduit 416 may be configured to permit gaseous or liquid fluid to leave the chamber 418.

With reference to FIGS. 7F-7H, example embodiments of the the hopper 402 and the receptacle 403 will be described in further detail. As illustrated, the receptacle 403 may include a taper 444 positioned between a first portion 446 and a second portion 448. The taper 444 may be configured to direct substances into a passage 438 of the shuttle 428. The first portion 446 may be sized and shaped to the receive substances. The taper 444 may narrow the receptacle 403 such that the second portion 448 may be smaller than the first portion 446. For example, the second portion 448 may include one or more dimensions less than corresponding dimensions of the first portion 446. As illustrated for example in FIG. 7F, the second portion 448 of the receptacle 403 may be sized and/or shaped to correspond to the passage 438 of the shuttle 428. For example, the second portion 448 may include one or more dimensions substantially the same as corresponding dimensions of the passage 438 of the shuttle 428. Such configurations may facilitate directing substances into the passage 438 of the shuttle 428.

As illustrated in FIG. 7F, the chamber 418 may be defined between the window 84 of the interface assembly 80 and the shuttle 428. Specifically, in the illustrated configuration, the chamber 418 is defined at least partially by the window 84 and the shuttle 428. Substances positioned over the window 84 in the chamber 418 may be analyzed and/or processed by the head assembly 70 via the interface assembly 80.

The size and/or shape of the chamber 418 may determine how much substance may enter the chamber 418 to be analyzed and/or processed. As illustrated for example in FIG. 7F, the chamber 418 may include a dimension W that may contribute to determining how much substance may enter the chamber 418 to be analyzed and/or processed. The size of dimension W may be varied to control the volume of substance that may enter the chamber 418.

As indicated by the arrows of the inlet conduit 412 and the outlet conduit 416 in FIG. 7F, gaseous or liquid fluid may be directed through the inlet conduit 412, the chamber 418 and the outlet conduit 416 to evacuate the chamber 418. For example, fluid (e.g., air, etc.) may be directed through the chamber 418 via the inlet conduit 412 and the outlet conduit 416 to remove samples positioned inside of the chamber 418. In another example, fluid may be directed through the chamber 418 to remove undesired substances such as contaminants from the chamber 418. In yet another example, a pressure differential generated downstream of the outlet conduit 416 may evacuate the chamber 418 by way of the inlet conduit 412 and the outlet conduit 416. In non-illustrated configurations, the inlet conduit 412 may be omitted and the chamber 418 may be evacuated via the passage 438 of the shuttle 428.

As illustrated for example in FIGS. 7C-7E, the shuttle 428 may define the passage 438 configured to permit substances from the hopper 402 to enter the chamber 418. Turning to FIGS. 7G-7H, the passage 438 may include a taper 464 positioned between a first portion 466 and a second portion 468. The first portion 466 may be sized and shaped to the receive substance 450 from the receptacle 403 of the hopper 402. For example, the first portion 466 of the passage 438 may be sized and/or shaped to correspond to the second portion 448 of the receptacle 403. As illustrated for example in FIG. 7F, the first portion 466 of the passage 438 may include one or more dimensions substantially the same as a corresponding dimension of the second portion 448 of the receptacle 403. Turning back to FIGS. 7G-7H, the first portion 466 of the passage 438 may include one or more dimensions substantially less than a corresponding dimension of the second portion 448 of the receptacle 403. The taper 464 may narrow the passage 438 such that the second portion 468 may be smaller than the first portion 466. For example, the second portion 468 may include one or more dimensions less than corresponding dimensions of the first portion 466.

As illustrated for example in FIGS. 7E and 7H, in some configurations, the passage 438 of the shuttle 428 may be sized and shaped to correspond with the size and shape of the chamber 418. Such configurations may facilitate directing substances into the chamber 418 via the passage 438 of the shuttle 428. Some configurations of the passage 438 with respect to the chamber 418 may permit samples to enter the chamber 418 via the passage 438 while facilitating minimization of aggregation, segregation, and/or agglomeration in the sample and/or analyte.

Specifically, the second portion 468 of the passage 438 may be sized and/or shaped to correspond to the chamber 418. In some configurations, the passage 438 may include one or more dimensions corresponding to one or more dimensions of the chamber 418. For example, the passage 438 may be sized and shaped to include one or more dimensions less than, substantially the same as, or greater than one or more dimensions of the chamber 418. In some configurations, the passage 438 may include a cross-sectional area corresponding to a cross-sectional area of the chamber 418. For example, the passage 438 may be sized and shaped to include a cross-sectional area less than, substantially the same as, or greater than a cross-sectional area of the chamber 418. In some configurations, the passage 438 may include a volume corresponding to a volume of the chamber 418. For example, the passage 438 may be sized and shaped to include a volume less than, substantially the same as, or greater than the volume of the chamber 418.

As discussed above, the actuator 422 may drive the shuttle 428 along the direction of movement S. With attention to FIGS. 7H-7G for example, the movement of the shuttle 428 will be discussed in further detail. The actuator 422 may drive the shuttle 428 between a first position illustrated for example in FIG. 7G, and a second position illustrated for example in FIG. 7H. In the position illustrate in FIG. 7G, the substance 450 may not be permitted to travel through the passage 438 and into the chamber 418 over the window 84 of the interface assembly 80. In the position of FIG. 7H, substance 450 may travel through the passage 438 and over the window 84 to be analyzed and/or processed. Accordingly, when the shuttle 428 is positioned in the position of FIG. 7H, the passage 438 permits a portion of substance 450 in the hopper 402 to enter the chamber 418 and when the shuttle 428 is positioned in the position of FIG. 7G, substance 450 in the hopper 402 does not enter the chamber 418 because the chamber 418 is covered by the body of the shuttle 428. In the first position of the shuttle 428 (see for example FIG. 7G), the passage 438 may not be aligned with the chamber 418. In such positions, the chamber 418 may be occluded by the shuttle 428 such that substance 450 may not travel into the chamber 418. In the second position of the shuttle 428 (see for example FIG. 7H), the passage 438 may be at least partially aligned with the chamber 418 to permit substance 450 to enter the chamber 418. The movement of the shuttle 428 may permit granular sample portions such as substance 450 to incrementally enter the chamber 418 to be analyzed. Specifically, the repeated movement of the shuttle 428 may apportion granular samples such as substance 450 to be analyzed.

As illustrated for example in FIG. 7D, the device 400 may include a detector 430 configured to detect at least one position of the shuttle 428. The detector 430 may be part of an interlock mechanism configured to disable operation of portions of the system 40 when the shuttle 428 is in certain positions. For example, the interlock mechanism may disable emitters such as the emitters 96 of the interface assembly 80 and/or the emitter assembly 62 inside of the housing 42. In some configurations, the detector 430 may be configured to detect when the shuttle 428 is in the first position to disable operation of portions of the system 40 when the shuttle 428 is in the first position. Additionally or alternatively, the detector 430 may be configured to detect when the shuttle 428 is in the second position to enable operation of portions of the system 40 when the shuttle 428 is in the second position. In some configurations, the detector 430 may be configured to enable and/or disable the head assembly 70.

In operation, the electronic assembly 420 and/or other portions of the system 40 may be configured to actuate the actuator 422 to move the shuttle 428 into a loading position. This may permit the substance to flow out of the passage 438 of the shuttle 428 into the chamber 418 over the window 84. In the loading position, the detector 430 may be configured to break the current to one or more emitters.

Additionally or alternatively, the electronic assembly 420 and/or other portions of the system 40 may be configured to actuate the actuator 422 to move the shuttle 428 into a scanning position. This blocks the flow of the substance into the chamber 418 over the window 84. This may isolate the substance over the window 84 in the chamber 418. In the scanning position, the detector 430 may be configured to allow current to flow to one or more emitters. The system 40 may be configured to analyze and/or process the substance in the second scanning position, for example, with the head assembly 70.

As discussed above, the inlet conduit 412 and the outlet conduit 416 may be configured to permit gaseous or liquid fluid to pass through the body portion 434 to the chamber 418 to evacuate and/or purge the substance from the chamber 418 after the substance is analyzed and/or processed. The inlet 410 and/or the outlet 414 may be connected to, for example, a vacuum line, a fluid line and/or a gas line to facilitate evacuation and/or purging of the substance.

In some configurations, after the substance is evacuated and/or purged from the chamber 418, the contents of the chamber 418 may be analyzed to determine whether the substance has been fully or sufficiently evacuated and/or purged. For example, the head assembly 70 may analyze the contents of the chamber 418. In some configurations, the substance may be evacuated via the outlet conduit 416 into a sample container for further processing and/or analysis. In other configurations, the substance may be evacuated via the outlet conduit 416 and discarded.

Additionally or alternatively, the electronic assembly 420 and/or other portions of the system 40 may be configured to actuate the actuator 422 to move the shuttle 428 back into the loading position. The above-mentioned process can be repeated until all of the substance positioned in the hopper 402 has been analyzed and/or processed. In some configurations, the head assembly 70 may be used to determine that no substance is left in the hopper 402. In some configurations, the device 400 may be operated automatically by the electronic assembly 420 and/or other portions of the system 40. In such configurations, processors of the electronic assembly 420 and/or other portions of the system 40 may be configured to execute instructions such that the device 400 and/or the system 40 performs any combination or all of the steps described above.

The shuttle 428 may include any suitable configurations to apportion the substance 450 to be analyzed. For example, in alternative configurations the shuttle 428 may include a gate that opens and closes to incrementally permit samples such as the substance 450 to be analyzed. In another example, the shuttle 428 may be a rotating member such as a gear with boundary members configured to separate samples into portions to be analyzed. In such configurations, the boundary members may define one or more compartments that receive a portion of the samples to be incrementally analyzed. Although in the illustrated configuration the shuttle 428 is actuated in one direction of movement, in other configurations the shuttle 428 may be actuated in any suitable number of directions of movement (linear, angular, etc.) to apportion samples to be incrementally analyzed. In some configurations, only a portion of the shuttle 428, such as a gate or a boundary member, may be actuated to apportion samples. Additionally or alternatively, in some configurations the shuttle 428 may be actuated to deliver samples to be analyzed, for example, over the window 84. In such configurations, the shuttle 428 may apportions samples to be analyzed, the shuttle 428 may be actuated over the window 84 and release the sample portions to be analyzed.

Figure 8A:
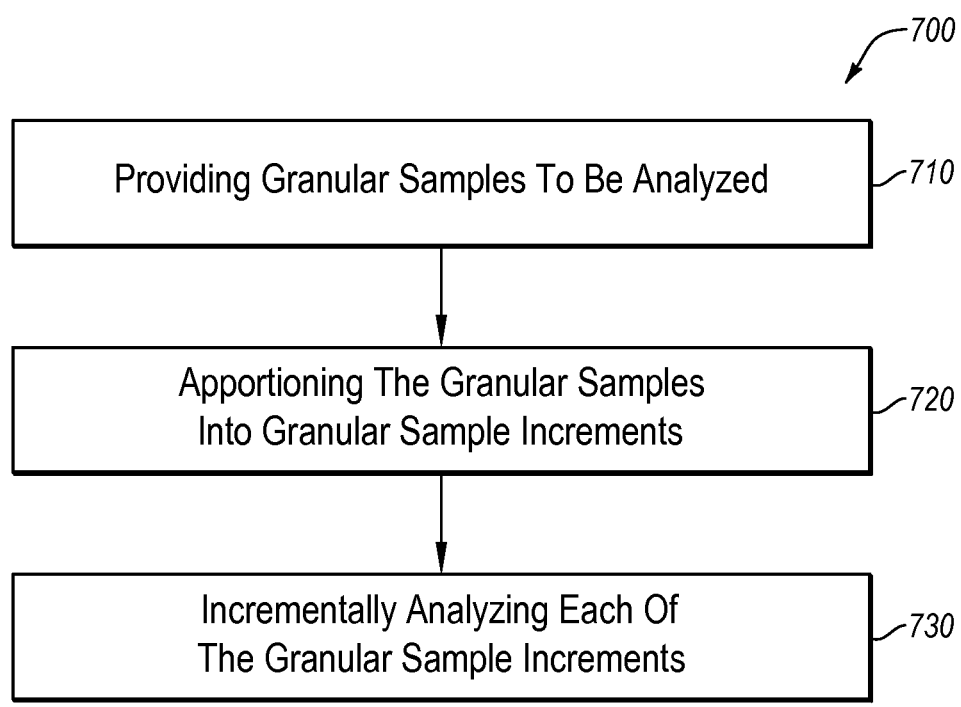
FIGS. 8A and 8B illustrate example configurations of a method.
Figure 8B:
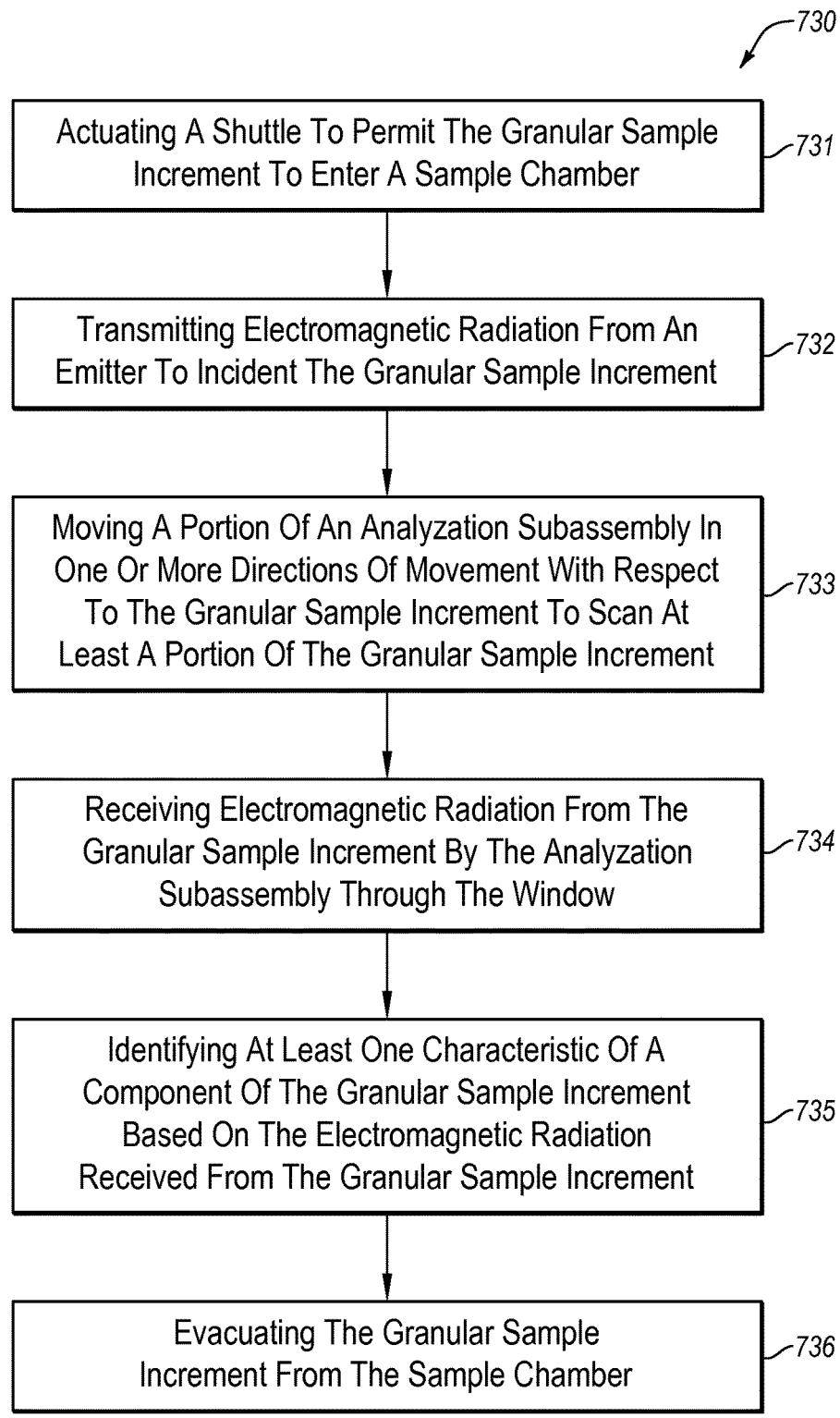

With reference to FIGS. 8A-8B, a method 700 of analyzing granular samples will be described in further detail. In some configurations, the method 700 may be implemented by the system 40 with the device 400. Although the method 700 will be described with respect to the system 40 and the device 400, it should be appreciated that the method 700 may be implemented in other manners and/or with other embodiments.

As illustrated for example in FIG. 8A, the example method 700 may include a step 710 of providing granular samples to be analyzed. The method 700 may include a step 720 of apportioning the granular samples into granular sample increments. The method 700 may include a step 730 of incrementally analyzing each of the granular sample increments.

Turning to FIG. 8B, the method 700 will be described in further detail. Specifically, an example configuration of the step 730 of the method 700 will be described in further detail. As illustrated, the step 730 of incrementally analyzing each of the granular sample increments may include a step 731 of actuating a shuttle to permit the granular sample increment to enter a sample chamber; a step 732 of transmitting electromagnetic radiation from an emitter to incident the granular sample increment; a step 733 of moving a portion of an analyzation subassembly in one or more directions of movement with respect to the granular sample increment to scan at least a portion of the granular sample increment; a step 734 of receiving electromagnetic radiation from the granular sample increment by the analyzation subassembly; a step 735 of identifying at least one characteristic of a component of the granular sample increment based on the electromagnetic radiation received from the granular sample increment; and/or a step 736 of evacuating the granular sample increment from the sample chamber. The method 700 may include any suitable aspects described above, for example, with respect to FIGS. 7A-7H.

Figure 9A:
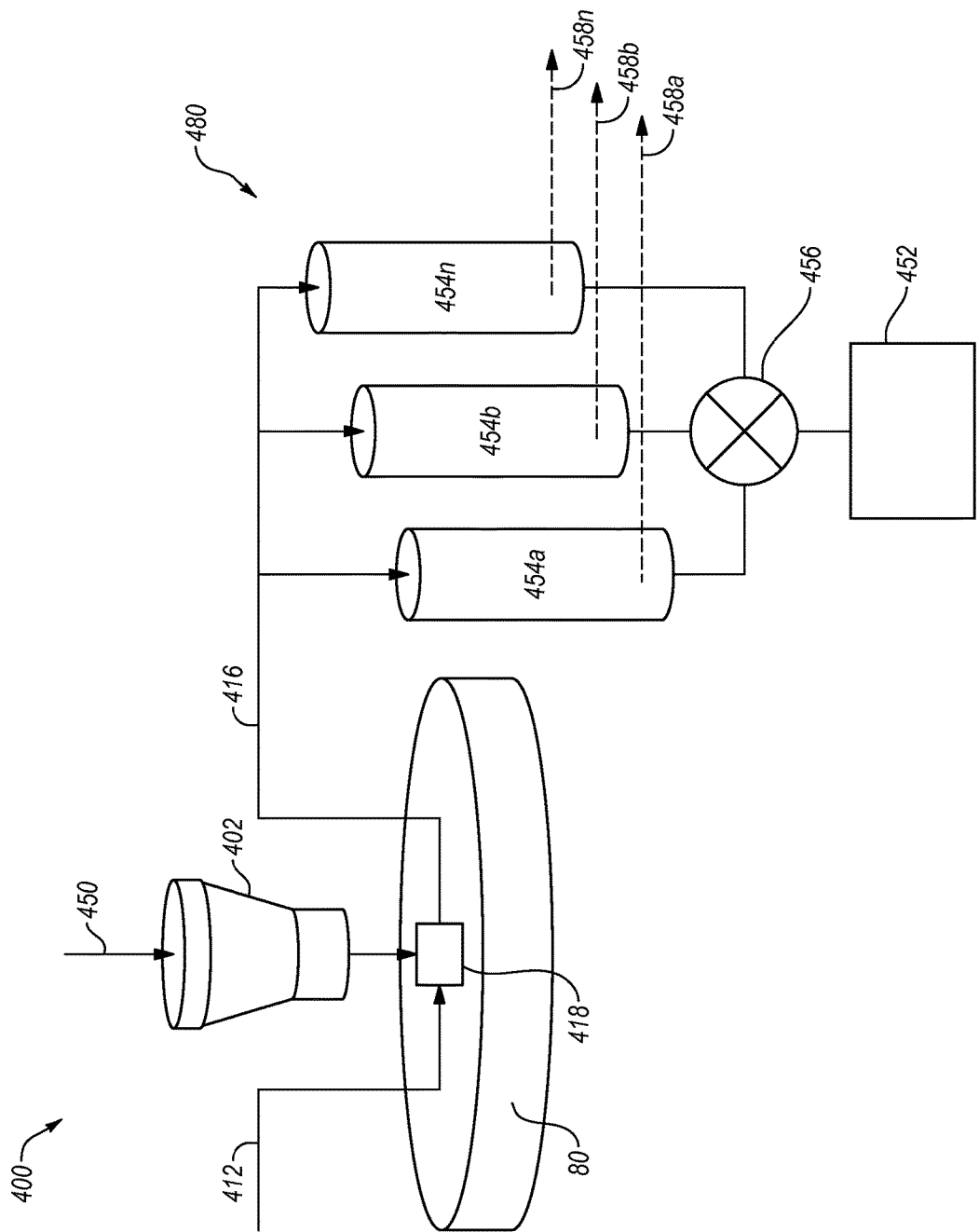
FIG. 9A is a schematic diagram of the device of FIGS. 7A-7B with an evacuation subassembly.

FIG. 9A illustrates a schematic representation of the device 400 with additional aspects and/or components illustrated. Specifically, the device 400 may include an evacuation subassembly 480. With attention to FIG. 8, additional aspects of the system 40 including the evacuation subassembly 480 will be discussed. As illustrated, the substance 450 may be positioned in the hopper 402 which may direct the substance 450 into the chamber 418 positioned over the interface assembly 80, as described above. The inlet conduit 412 and the outlet conduit 416 may be in fluid connection with the chamber 418 and permit the substance 450 to be evacuated and/or purged from the chamber 418. A vacuum element 452 such as a compressor, blower, pump, or vacuum may generate a pressure differential to evacuate and/or purge the substance 450. The device 400 may include a switch 456 configured to selectively couple the vacuum 452 to one or more vessels 454a, 454b . . . 454n. The device 400 may include any suitable number of vessels 454a-454n. The vessels 454a-454n may be configured to retain portions of the substance 450 evacuated and/or purged from the chamber 418. One or more of the vessels 454a-454n may include outlets 458a, 458b . . . 458n corresponding to the one or more vessels 454a, 454b . . . 454n. The outlets 458a-458n may permit portions of the substance 450 in corresponding vessels 454a-454n to be continuously or incrementally removed from the vessels 454a-454n. One or more of the outlets 458a-458n may be coupled to a disposal to permit substance in one or more of the vessels 454a-454n to be disposed.

As illustrated in FIG. 8, the device 400 may be configured to aggregate and/or concentrate one or more components of the substance 450. Specifically, the switch 456 may be selectively coupled to one of the vessels 454a-454n to aggregate and/or concentrate one or more components of the substance 450 in that one of the vessels 454a-454n. The switch 456 may be selectively coupled to one of the vessels 454a-454n based on data from analyzing the substance 450 by the head assembly 70 via the interface assembly 80.

Figure 9B:
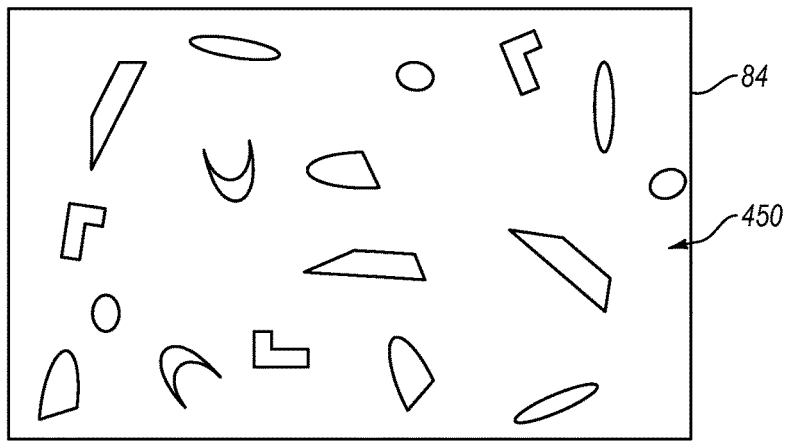
FIGS. 9B-9D are representations of data obtained during analysis of a sample by the system of FIGS. 2A-2B.
Figure 9C:
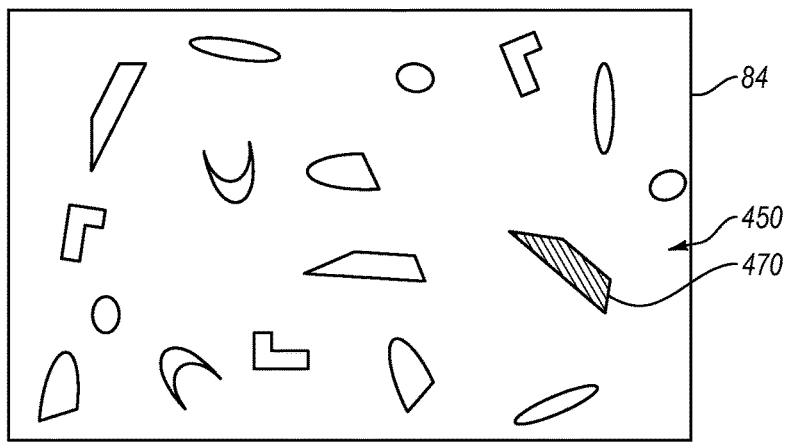
Figure 9D:
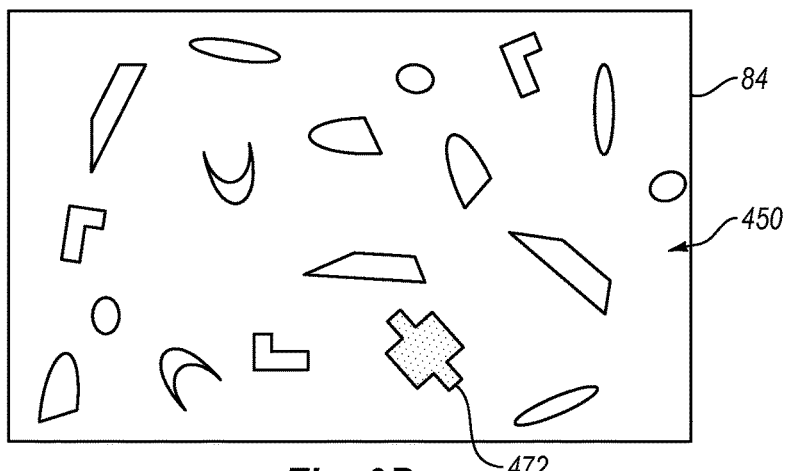

FIGS. 9B-9D illustrate representations of data obtained during analysis of a sample. As illustrated, a portion of the substance 450 may be positioned on or over the window 84. FIGS. 9B-9D may be visual representations of data obtained during analysis and/or processing of the substance 450 by the head assembly 70. Additionally or alternatively, FIGS. 9B-9D may represent visible light images of the substance 450 on the window 84. Additionally or alternatively, FIGS. 9B-9D may represent data obtained by way of imaging by electromagnetic radiation that is different than visible light radiation.

As illustrated in FIG. 9B, the substance 450 may include a plurality of particles. In some circumstances, the particles may include different characteristics from one another. For example, the particles may include different dimensions, shapes, chemical composition, etc. Data obtained during analysis of the substance 450 may be used to distinguish different particles based on their characteristics. The data may be used to identify various components of the substance 450. In some circumstances, the substance 450 may include contaminants that may be identified based on the data.

FIG. 9C illustrates a representation of the substance 450 with a first particle 470. The particle 470 may be any component of the substance 450, but in some circumstances the particle 470 may represent a contaminant or a desired component of the substance 450.

FIG. 9D illustrates a representation of the substance 450 with a second particle 472. The particle 472 may be any component of the substance 450, but in some circumstances the particle 472 may represent a contaminant or a desired component of the substance 450.

Data obtained during analysis of the substance 450 may be used to automatically or manually identify the particle 470 and/or the particle 472. Specifically, the system 40 may be configured to automatically or manually identify the particle 470 and/or the particle 472.

With collective reference to FIGS. 9A-9D, the operation of the example device 400 configured to aggregate and/or concentrate one or more components of the substance 450 will be described. The system 40 may analyze the substance 450 and obtain data regarding the substance 450. The system 40 may automatically determine characteristics of components and/or particles of the substance 450.

If the system 40 determines that the substance 450 does not include components and/or contaminants such as particles 470, 472 (as illustrated for example in FIGS. 9C and 9D), the system 40 may be configured to activate the switch 456 to couple the vacuum 452 to the vessel 454a. The vacuum 452 may evacuate the substance 450 from the chamber 418 into the vessel 454a. If the vessel 454a is connected to the outlet 458a, then the vacuum 452 may be configured to direct the substance 450 to the outlet 458a. If the outlet 458a is connected to a disposal, the substance 450 may be disposed. Alternatively, the substance 450 may be retained in the vessel 454a. In such configurations, the device 400 may be configured to aggregate and/or concentrate portions of the substance 450 without components and/or contaminants such as particles 470, 472 in the vessel 454a. For example, the above-mentioned process may be repeated for multiple portions of the substance 450 to aggregate and/or concentrate multiple portions of the substance 450 that do not include components and/or contaminants such as particles 470, 472 in the vessel 454a.

If the system 40 determines that the substance 450 includes one or more components and/or contaminants such as particle 470 (as illustrated for example in FIG. 9C), the system 40 may be configured to activate the switch 456 to couple the vacuum 452 to the vessel 454b. The vacuum 452 may evacuate the substance 450 with the particle 470 from the chamber 418 into the vessel 454b. If the vessel 454b is connected to the outlet 458b, then the vacuum 452 may be configured to direct the substance 450 with the particle 470 to the outlet 458b. If the outlet 458b is connected to a disposal, the substance 450 with the particle 470 may be disposed. Alternatively, the substance 450 with the particle 470 may be retained in the vessel 454b. In such configurations, the device 400 may be configured to aggregate and/or concentrate portions of the substance 450 with the particle 470 in the vessel 454b. For example, the above-mentioned process may be repeated for multiple portions of the substance 450 with components and/or contaminants such as the particle 470 to aggregate and/or concentrate multiple portions of the substance 450 that include components and/or contaminants such as the particle 470 in the vessel 454b. The aggregated and/or concentrated portions of the substance 450 may be retained for future analysis and/or processing.

If the system 40 determines that the substance 450 includes one or more components and/or contaminants such as particle 472 (as illustrated for example in FIG. 9D), the system 40 may be configured to activate the switch 456 to couple the vacuum 452 to the vessel 454n. The vacuum 452 may evacuate the substance 450 with the particle 472 from the chamber 418 into the vessel 454n. If the vessel 454n is connected to the outlet 458n, then the vacuum 452 may be configured to direct the substance 450 with the particle 472 to the outlet 458n. If the outlet 458n is connected to a disposal, the substance 450 with the particle 472 may be disposed. Alternatively, the substance 450 with the particle 472 may be retained in the vessel 454n. In such configurations, the device 400 may be configured to aggregate and/or concentrate portions of the substance 450 with the particle 472 in the vessel 454n. For example, the above-mentioned process may be repeated for multiple portions of the substance 450 with components and/or contaminants such as the particle 472 to aggregate and/or concentrate multiple portions of the substance 450 that include components and/or contaminants such as the particle 472 in the vessel 454n. The aggregated and/or concentrated portions of the substance 450 may be retained for future analysis and/or processing.

Figure 10A:
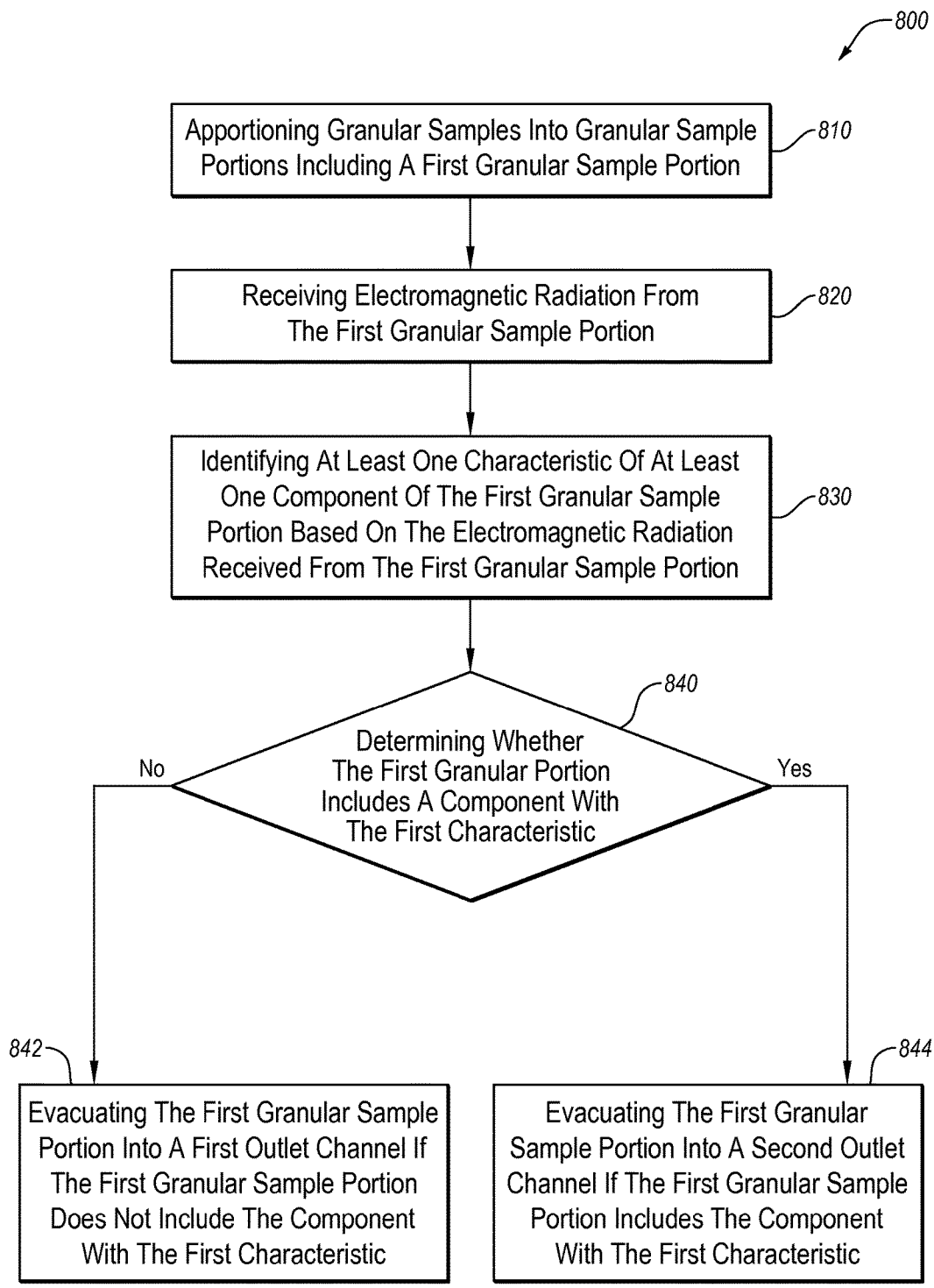
FIGS. 10A and 10B illustrate example configurations of a method.
Figure 10B:
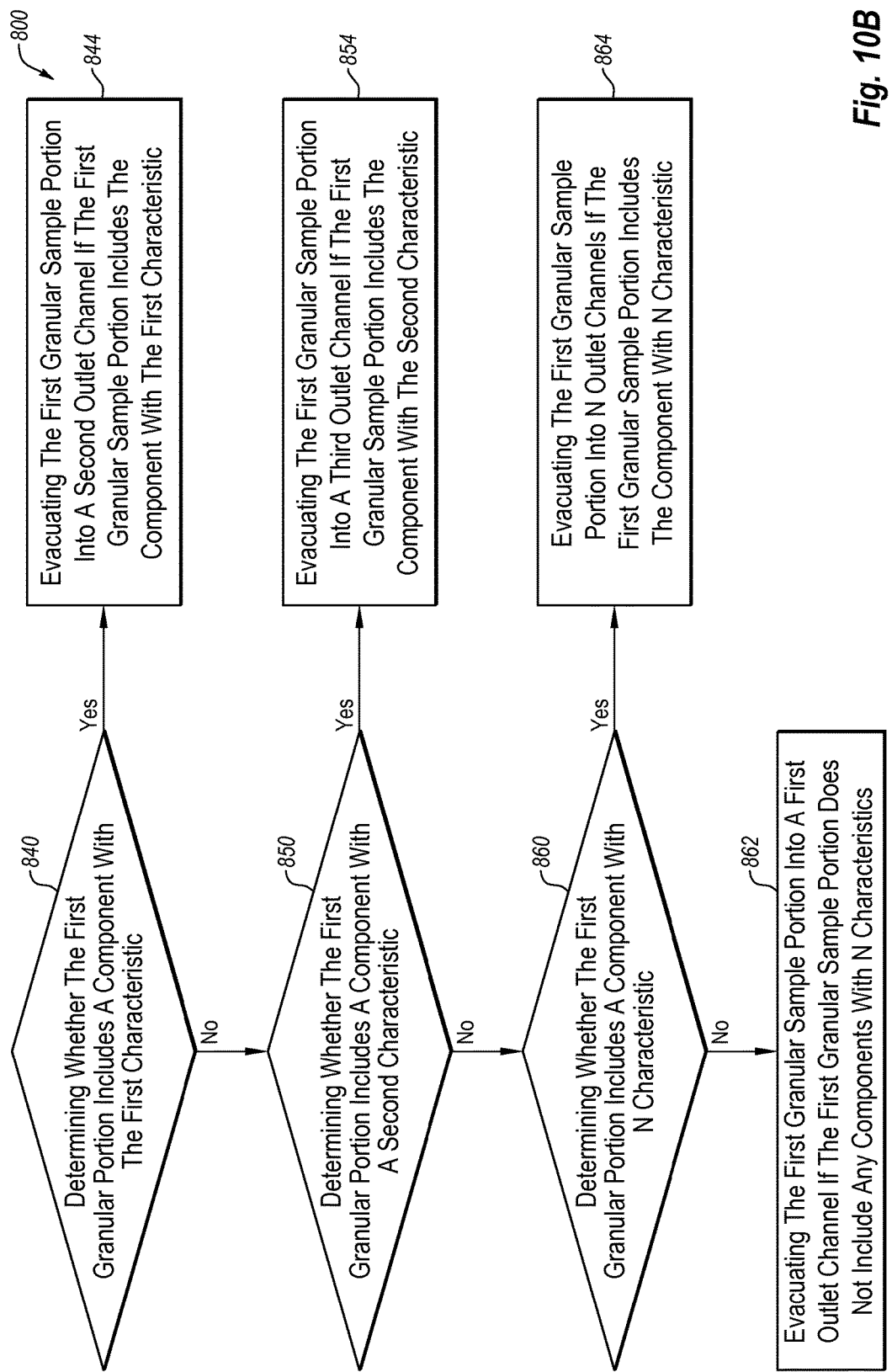

With reference to FIGS. 10A-10B, a method 800 of analyzing granular samples will be described in further detail. In some configurations, the method 800 may be implemented by the system 40 with the device 400 and/or the evacuation assembly 480. It should be appreciated that the method 800 may be implemented in other manners and/or with other embodiments.

As illustrated for example in FIG. 10A, the example method 800 may include a step 810 of apportioning the granular samples into granular sample portions including a first granular sample portion. The method 800 may include a step 820 of receiving electromagnetic radiation from the first granular sample portion. The method 800 may include a step 830 of identifying at least one characteristic of at least one component of the first granular sample portion based on the electromagnetic radiation received from the first granular sample portion. The method 800 may include a step 840 determining whether the first granular portion includes a component with the first characteristic. The method 800 may include a step 842 of evacuating the first granular sample portion into a first outlet channel if the first granular sample portion does not include the component with the first characteristic. The method 800 may include a step 844 evacuating the first granular sample portion into a second outlet channel if the first granular sample portion includes the component with the first characteristic.

Turning to FIG. 10B, the method 800 will be described in further detail. Specifically, an example configuration of the method 800 will be described in further detail. As illustrated, in some configurations the method 800 may proceed to step 850 after the step 840, rather step 842 as illustrated for example in FIG. 10A. As illustrated in FIG. 10B, the method 800 may include the step 850 of determining whether the first granular portion includes a component with a second characteristic. The method 800 may include the step 854 of evacuating the first granular sample portion into a third outlet channel if the first granular sample portion includes the component with the second characteristic. If the first granular sample portion does not include the component with the second characteristic, then the method may proceed to step 860. As illustrated, the method 800 may continue for any number of components of any number N of characteristics. Specifically, the method 800 may include step 860 of determining whether the first granular portion includes a component with n characteristic. The method 800 may include step 862 of evacuating the first granular sample portion into a first outlet channel if the first granular sample portion does not include any components with n characteristics. The method 800 may include step 864 of evacuating the first granular sample portion into N outlet channels if the first granular sample portion includes the component with N characteristic.

The method 800 may be used to concentrate one or more components with certain characteristics in a specified outlet channel. Additionally or alternatively, the method 800 may be used to filter components with certain characteristics from a specified outlet channel. The method 800 may be used to separate and/or sort portions of an analyzed sample based on one or more detected characteristics of a component. Additionally or alternatively, the method 800 may be implemented to separate and/or sort portions of an analyzed sample based on one or more characteristics that are absent from the sample portions. The method 800 may include any suitable aspects described above, for example, with respect to FIGS. 9A-9D.

FIGS. 11A-11D illustrate a sample positioned on the window 84. FIGS. 11A-11D may be visual representations of data obtained during analysis and/or processing of a sample by the head assembly 70. Additionally or alternatively, FIGS. 11A-11D may represent visible light images of a sample on the window 84. Additionally or alternatively, FIGS. 11A-11D may represent data obtained by way of imaging by electromagnetic radiation that is different than visible light radiation. With attention to FIGS. 11A-11D, a method of analyzing and/or processing a sample will be described in further detail.

Figure 11A:
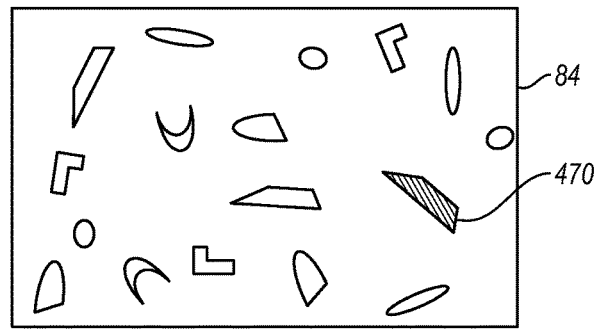
FIGS. 11A-11D are representations of scanning methods of the system of FIGS. 2A-2B.

As illustrated in FIG. 11A, a sample may include a plurality of particles. In some circumstances, the particles may include different characteristics from one another. For example, the particles may include different dimensions, shapes, chemical composition, etc. Data obtained during analysis of the sample may be used to distinguish different particles based on their characteristics. The data may be used to identify various components of the sample. In some circumstances, the sample may include contaminants that may be identified based on the data.

A method of analyzing and/or processing a sample may include scanning the sample using a first scanning method with a first electromagnetic radiation. In some configurations, the first electromagnetic radiation may be visible light resulting in analyzed data representing an image. FIG. 11A illustrates a representation of a sample with the first particle 470 that may be obtained using the first scanning method with the first electromagnetic radiation. The particle 470 may be any component of a sample, but in some circumstances the particle 470 may represent a contaminant or area of interest of a sample. Using the data obtained by the first scanning method with the first electromagnetic radiation, one or more contaminants and/or areas of interest of a sample may be identified. Identification may include the position and/or other characteristics of the contaminants and/or areas of interest.

After the contaminants and/or areas of interest (e.g., the particle 470, etc.) are identified, a second scanning method with a second electromagnetic radiation may be used to analyze and/or process the sample. In some configurations, the second scanning method may be Raman spectroscopy.

Figure 11B:
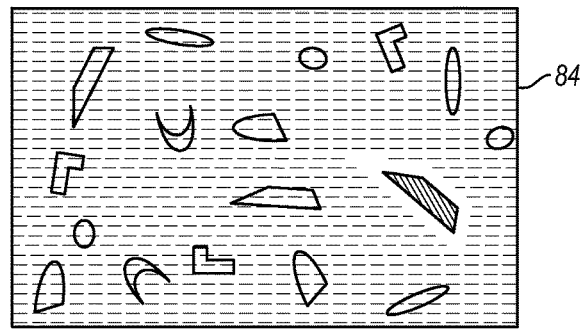

The second scanning method with the second electromagnetic radiation may be configured based on data obtained by the first scanning method with the first electromagnetic radiation. For example, as represented in FIG. 11B, the second scanning method may be configured such that certain portions of the sample (e.g., the particle 470, etc.) are not scanned. The portions of the sample that are not scanned may correspond with contaminants and/or areas of interest.

Figure 11C:
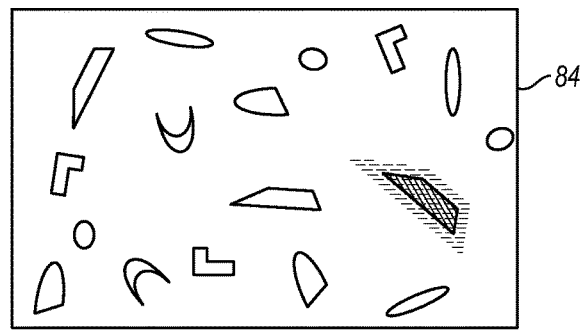

Additionally or alternatively, as represented in FIG. 11C, the second scanning method may be configured such that only certain portions of the sample (e.g., the particle 470, etc.) are scanned. The portions of the sample that are scanned may correspond with contaminants and/or areas of interest. The second scanning method may alter and/or modulate the characteristics of the sample. For example, the second electromagnetic radiation may burn or otherwise alter contaminants such as the particle 470.

Figure 11D:
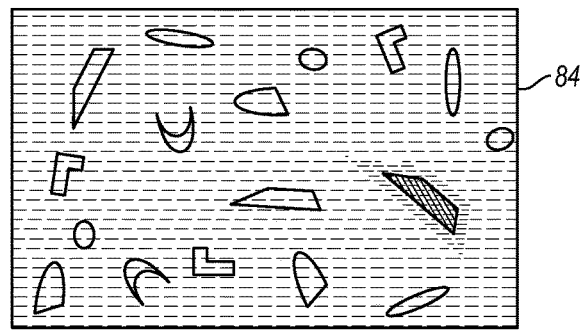

Additionally or alternatively, as represented in FIG. 11D, the second scanning method may be configured such that certain portions of the sample (e.g., the particle 470, etc.) are scanned with electromagnetic radiation with different characteristics.

In some configurations, a method of analyzing and/or processing a sample may include imaging a sample with electromagnetic radiation such as visible light and/or ultraviolet light. The method of analyzing and/or processing the sample may include analyzing the sample with Raman spectroscopy after imaging the sample. The method of analyzing and/or processing the sample may include configuring the Raman spectroscopy analyzation after imaging the sample and/or before Raman spectroscopy analyzation. Configuring the Raman spectroscopy analyzation may include identifying contaminants and/or areas of interest based on data obtained from imaging the sample. Configuring the Raman spectroscopy analyzation may include selecting portions of the sample to be analyzed by Raman spectroscopy and/or selecting portions of the sample not to be analyzed by Raman spectroscopy. Configuring the Raman spectroscopy analyzation may include selecting first portions of the sample to be analyzed by Raman spectroscopy of a first characteristic (e.g., power level, resolution, etc.) and/or selecting second portions of the sample different than the first portions to be analyzed by Raman spectroscopy of a second characteristic (e.g., power level, resolution, etc.). The method of analyzing and/or processing the sample may include analyzing the sample with Raman spectroscopy based on the configuration of the Raman spectroscopy analyzation.

Figure 12:
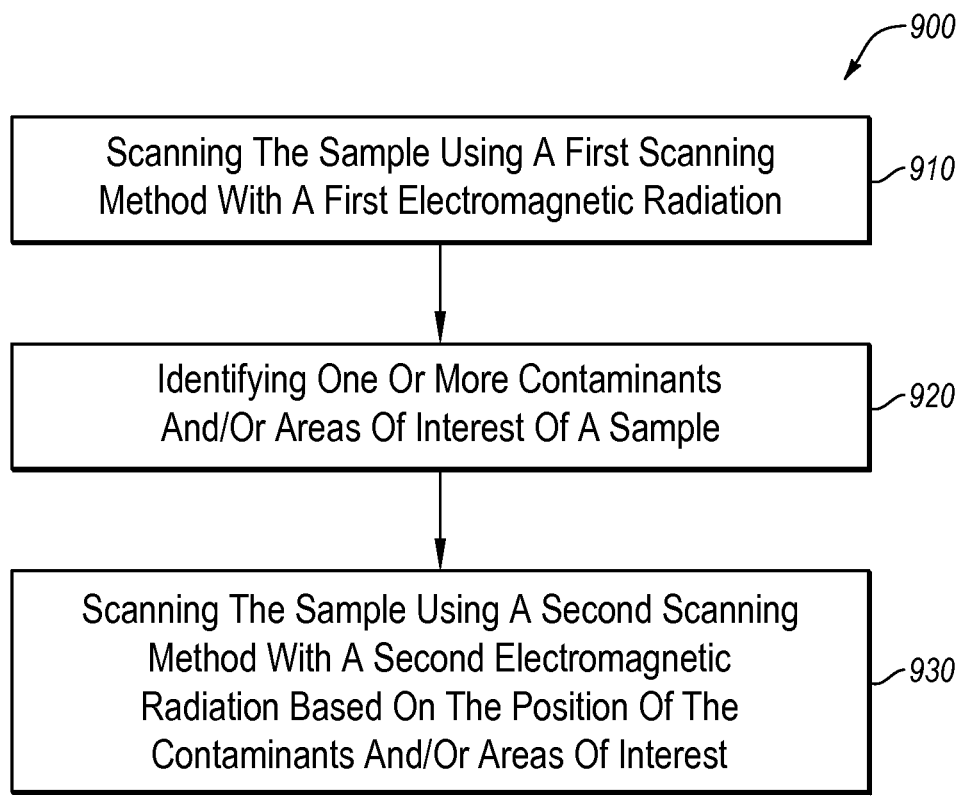
FIG. 12 illustrates an example configuration of a method.

With reference to FIG. 12, a method 900 method of analyzing and/or processing a sample will be described in further detail. In some configurations, the method 900 may be implemented by the system 40. It should be appreciated that the method 900 may be implemented in other manners and/or with other embodiments. As illustrated for example in FIG. 12, the example method 900 may include a step 910 of scanning the sample using a first scanning method with a first electromagnetic radiation. The method 900 may include a step 920 of identifying one or more contaminants and/or areas of interest of a sample. The method 900 may include a step 930 of scanning the sample using a second scanning method with a second electromagnetic radiation based on the position of the contaminants and/or areas of interest. The method 900 may include any suitable aspects described above.

Aspects of the present disclosure may be embodied in other forms without departing from its spirit or characteristics. The described aspects are to be considered in all respects illustrative and not restrictive. All changes which come within the meaning and range of equivalency of the claims are to be embraced within their scope.

What is claimed is:

1. A system comprising:
    a device for apportioning granular samples comprising:
        a sample feeder defining a conduit, the conduit including a first opening to receive the granular samples and a second opening;
        a shuttle operably coupled to the sample feeder to receive the granular samples from the conduit via the second opening, the shuttle configured to apportion the granular samples to incrementally enter a sample chamber to be analyzed; and
        an outlet conduit fluidly coupled to the sample chamber and configured to permit the sample chamber to be evacuated; and
    a hyperspectral analyzation subassembly electromagnetically coupled to the device, the hyperspectral analyzation subassembly configured to obtain information for at least portions of the granular samples in the sample chamber, the hyperspectral analyzation subassembly comprising:
        one or more emitters configured to generate electromagnetic radiation electromagnetically coupled to the sample chamber;
        one or more sensors configured to detect electromagnetic radiation electromagnetically coupled to the sample chamber;
        an electromagnetically transmissive window defining at least a portion of the sample chamber, wherein at least one of the one or more sensors is configured to detect electromagnetic radiation from the sample chamber via the window; and
        an analyzation actuation subassembly configured to actuate at least a portion of the hyperspectral analyzation subassembly in one or more directions of movement with respect to the sample chamber.

2. The system of claim 1, the device further comprising an actuation subassembly configured to actuate the shuttle in one or more directions of movement, the actuation subassembly comprising:
    a first actuator configured to actuate the shuttle in a first direction of movement between a first position and a second position; and
    a first slide configured to permit the shuttle to be moved between the first position and the second position;
    wherein the shuttle positioned in the first position does not permit the granular sample portions to enter the sample chamber, and the shuttle positioned in the second position permits at least one of the granular sample portions to enter the sample chamber.

3. The system of claim 2, wherein the shuttle at least partially defines a shuttle passage sized and shaped to correspond with the size and shape of the sample chamber.

4. The system of claim 3, wherein the shuttle passage extends at least partially through the shuttle.

5. The system of claim 1, further comprising an evacuation subassembly fluidly coupled to the outlet conduit and comprising:
    one or more vacuum elements configured to generate a pressure differential to evacuate the sample chamber; and
    a switch configured to selectively couple the one or more vacuums to one or more outlet channels to selectively evacuate the sample chamber into one or more outlet channels;
    wherein the sample chamber is selectively evacuated based on one or more characteristics of at least one component of a substance detected or not detected inside of the sample chamber.

6. The system of claim 1, further comprising a hopper coupled to the sample feeder and configured to direct the granular samples into the sample feeder.

7. The system of claim 1, wherein,
    the analyzation actuation subassembly further comprises:
        a first actuator configured to actuate at least the portion of the hyperspectral analyzation subassembly in a first direction of movement,
        a second actuator configured to actuate at least the portion of the hyperspectral analyzation subassembly in a second direction of movement, and
        a third actuator configured to actuate at least the portion of the hyperspectral analyzation subassembly in a third direction of movement; and
    the hyperspectral analyzation subassembly further comprises:
        an optical multiplexer electromagnetically coupled to the objective, wherein the optical multiplexer is configured to direct electromagnetic radiation between the sample chamber and at least one of the one or more sensors, at least one of the one or more emitters, or both at least one of the one or more sensors at least one of the one or more emitters; and
        an objective electromagnetically coupled between the window and the optical multiplexer, the objective configured to focus electromagnetic radiation travelling to or from the sample chamber.

8. A method of analyzing granular samples comprising:
    providing the system of claim 1;
    providing granular samples to be analyzed to the conduit of the sample feeder;
    apportioning the granular samples into granular sample increments; and
    incrementally analyzing each of the granular sample increments, comprising, for each granular sample increment:
        actuating the shuttle to permit a granular sample increment to enter the sample chamber at least partially defined by the electromagnetically transmissive window;
        transmitting electromagnetic radiation from at least one of the one or more emitters to the granular sample increment;
        moving a portion of the analyzation subassembly in the one or more directions of movement with respect to the granular sample increment to scan at least a portion of the granular sample increment;
        receiving electromagnetic radiation from the granular sample increment by at least one of the one or more sensors through the electromagnetically transmissive window;

identifying at least one characteristic of a component of the granular sample increment based on the received electromagnetic radiation; and evacuating the granular sample increment from the sample chamber.

9. The method of claim 8, wherein receiving the electromagnetic radiation from the granular sample increment comprises receiving the electromagnetic radiation at a sensor of the one or more sensors, wherein the sensor is configured to generate signals based on the received electromagnetic radiation.

10. The method of claim 9, further comprising analyzing the signals to generate a representation of at least a portion of the granular sample increment.

11. The method of claim 10, further comprising identifying at least one component of the granular sample increment based on the signals.

12. The method of claim 8, wherein the granular samples comprise pharmaceutical micro-structured blends of substances.

13. The system of claim 1, wherein at least one of the one or more emitters generates visible, ultraviolet, X-ray, terahertz, or infrared radiation.

14. The system of claim 1, wherein at least one of the one or more emitters is a Raman laser source.

15. The system of claim 1, wherein at least one of the one or more sensors is configured to detect fluorescence or reflection.

16. The system of claim 1, wherein at least one of the one or more sensors is a Raman spectrometer.

* * * * *